US012790444B2

(12) United States Patent
Bisker et al.

(10) Patent No.: US 12,790,444 B2
(45) Date of Patent: Nov. 10, 2026

(54) DENDRON-POLYMER HYBRIDS AS TAILORABLE CORONAE OF SINGLE-WALLED CARBON NANOTUBES AND USES THEREOF

(71) Applicant: Ramot at Tel-Aviv University Ltd., Tel Aviv (IL)

(72) Inventors: Gili Hana Bisker, Tel Aviv (IL); Roey Jacob Amir, Tel Aviv (IL); Verena Wulf, Tel Aviv (IL); Gadi Slor, Tel Aviv (IL); Parul Rathee, Tel Aviv (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 704 days.

(21) Appl. No.: 18/190,517

(22) Filed: Mar. 27, 2023

(65) Prior Publication Data

US 2023/0303779 A1 Sep. 28, 2023

Related U.S. Application Data

(60) Provisional application No. 63/324,375, filed on Mar. 28, 2022.

(51) Int. Cl.

| | |
|---|---|
| ***C08G 83/00*** | (2006.01) |
| ***B82Y 5/00*** | (2011.01) |
| ***C01B 32/159*** | (2017.01) |
| ***G01N 33/533*** | (2006.01) |
| ***G01N 33/535*** | (2006.01) |

(52) U.S. Cl.

CPC .............. *C08G 83/004* (2013.01); *B82Y 5/00* (2013.01); *C01B 32/159* (2017.08); *G01N 33/533* (2013.01); *G01N 33/535* (2013.01); *C01P 2004/13* (2013.01)

(58) Field of Classification Search

CPC .................................................... A61K 9/0092

See application file for complete search history.

(56) References Cited

U.S. PATENT DOCUMENTS

| | | | |
|---|---|---|---|
| 9,664,677 | B2 | 5/2017 | Strano |
| 10,837,045 | B2 | 11/2020 | Reuel |
| 10,869,939 | B2 | 12/2020 | Amir |

(Continued)

FOREIGN PATENT DOCUMENTS

WO 2021240516 A1 12/2021

OTHER PUBLICATIONS

Abidian et al, Adv Mater. Feb. 17, 2006; 18(4): 405â409. doi:10.1002/adma.200501726. (Year: 2006).*

(Continued)

*Primary Examiner* — Benjamin J Packard

(74) *Attorney, Agent, or Firm* — Roach Brown McCarthy & Gruber, P.C.; Kevin D. McCarthy

(57) ABSTRACT

The present invention relates to highly modular amphiphilic polymer-dendron hybrids comprising hydrophobic dendrons conjugated to hydrophilic polymers that can be synthesized with a high degree of structural freedom, for suspending SWCNTs in aqueous solution. Utilizing the susceptibility of the polymer-dendrons towards enzymatic degradation, the present invention provides methods of detecting the presence of an enzyme in a sample as well as methods of monitoring of enzymatic activity by changes in the SWCNT fluorescent signal.

20 Claims, 26 Drawing Sheets

(56) References Cited

U.S. PATENT DOCUMENTS

2018/0356414 A1 12/2018 Strano

OTHER PUBLICATIONS

Amir et al., (2021) Oncometabolite Fingerprinting Using Fluorescent Single-Walled Carbon Nanotubes. Advanced Materials Interfaces 9(4): 2101591; 8 pages.
Bahun and Adronov (2010) Interactions of carbon nanotubes with pyrene-functionalized linear-dendritic hybrid polymers. Journal of Polymer Science Part A: Polymer Chemistry 48(5): 1016-1028.
Bisker et al., (2018) Insulin Detection Using a Corona Phase Molecular Recognition Site on Single-Walled Carbon Nanotubes. ACS Sens 3(2): 367-377.
Bisker et al., (2016) Protein-targeted corona phase molecular recognition. Nature Communications 7: 10241; 14 pages.
Chio et al., (2019) Electrostatic Assemblies of Single-Walled Carbon Nanotubes and Sequence-Tunable Peptoid Polymers Detect a Lectin Protein and Its Target Sugars. Nano Lett 19(11): 7563-7572.
Cho et al., (2021) Antibody-Free Rapid Detection of SARS-CoV-2 Proteins Using Corona Phase Molecular Recognition to Accelerate Development Time. Anal Chem 93(44): 14685-14693.
Dong et al., (2020) A synthetic mimic of phosphodiesterase type 5 based on corona phase molecular recognition of single-walled carbon nanotubes. Proc Natl Acad Sci U S A 117(43): 26616-26625.
Ehrlich et al., (2021) Optical Nanosensors for Real-Time Feedback on Insulin Secretion by β-Cells. Small 17(30): e2101660; 12 pages.
Ernst et al., (2013) Functional Surfactants for Carbon Nanotubes: Effects of Design. J Phys Chem C 117(2): 1157-1162.
Ernst et al., (2017) Noncovalent Stable Functionalization Makes Carbon Nanotubes Hydrophilic and Biocompatible. J Phys Chem C 121(34): 18887-18891.
Fagan (2019) Aqueous two-polymer phase extraction of single-wall carbon nanotubes using surfactants. Nanoscale Adv 1(9): 3307-3324.
Gao et al., (2013) Effect of medium dielectric constant on the physical properties of single-walled carbon nanotubes. Chemical Physics 413: 35-38.
Gillen and Boghossian (2019) Non-covalent Methods of Engineering Optical Sensors Based on Single-Walled Carbon Nanotubes. Frontiers in chemistry 7: 612; pp. 1-13.
Gitsov (2008) Hybrid linear dendritic macromolecules: From synthesis to applications. Journal of Polymer Science Part A: Polymer Chemistry 46(16): 5295-5314.
Gutierrez-Ulloa et al., (2018) Carbon Nanotubes Decorated with Cationic Carbosilane Dendrons and Their Hybrids with Nucleic Acids. ChemNanoMat 4(2): 220-230.
Harnoy et al., (2014) Enzyme-Responsive Amphiphilic PEG-Dendron Hybrids and Their Assembly into Smart Micellar Nanocarriers. J Am Chem Soc 136(21): 7531-7534.
Harnoy et al., (2017) Modular Synthetic Approach for Adjusting the Disassembly Rates of Enzyme-Responsive Polymeric Micelles. Biomacromolecules 18(4): 1218-1228.
Harvey et al., (2017) A Carbon Nanotube Reporter of miRNA Hybridization Events In Vivo. Nat Biomed Eng 1: 0041; pp. 1-11.
Heller et al., (2011) Peptide secondary structure modulates single-walled carbon nanotube fluorescence as a chaperone sensor for nitroaromatics. Proc Natl Acad Sci U S A 108(21): 8544-8549.
Hendler-Neumark and Bisker (2019) Fluorescent Single-Walled Carbon Nanotubes for Protein Detection. Sensors (Basel 19(24): 5403; pp. 1-16.
Hertel et al., (2005) Spectroscopy of single- and double-wall carbon nanotubes in different environments. Nano Lett 5(3): 511-514.
Jeong et al., (2019) High-throughput evolution of near-infrared serotonin nanosensors. Sci Adv 5(12): eaay3771; pp. 1-13.
Kruss et al., (2014) Neurotransmitter detection using corona phase molecular recognition on fluorescent single-walled carbon nanotube sensors. J Am Chem Soc 136(2): 713-724.
Kuang et al., (2021) Charge Transfer from Photoexcited Semiconducting Single-Walled Carbon Nanotubes to Wide-Bandgap Wrapping Polymer. J Phys Chem C 125(15): 8125-8136.
Lambert et al., (2019) Directed evolution of the optoelectronic properties of synthetic nanomaterials. Chem Commun (Camb) 55(22): 3239-3242.
Lee et al., (2020) Implantable Nanosensors for Human Steroid Hormone Sensing In Vivo Using a Self-Templating Corona Phase Molecular Recognition. Advanced Healthcare Materials 9(21): 2000429; 13 pages.
Maeda et al., (2018) Control of near infrared photoluminescence properties of single-walled carbon nanotubes by functionalization with dendrons. Nanoscale 10(48): 23012-23017.
Papadopoulos et al., (2021) Efficient charge-transfer from diketopyrrolopyrroles to single-walled carbon nanotubes. Nanoscale 13: 11544-11551.
Park et al., (2019) Measuring the Accessible Surface Area within the Nanoparticle Corona Using Molecular Probe Adsorption. Nano Lett 19(11): 7712-7724.
Pinals et al., (2021) Rapid SARS-CoV-2 Spike Protein Detection by Carbon Nanotube-Based Near-Infrared Nanosensors. Nano Lett 21(5): 2272-2280.
Roxbury et al., (2011) Recognition ability of DNA for carbon nanotubes correlates with their binding affinity. Langmuir 27(13): 8282-8293.
Salem et al., (2016) Chirality dependent corona phase molecular recognition of DNA-wrapped carbon nanotubes. Carbon 97: 147-153.
Segal et al., (2017) Molecular Precision and Enzymatic Degradation: From Readily to Undegradable Polymeric Micelles by Minor Structural Changes. J Am Chem Soc 139(2): 803-810.
Setaro et al., (2010) Polyglycerol-derived amphiphiles for single walled carbon nanotube suspension. Chemical Physics Letters 493(1-3): 147-150.
Shumeiko et al., (2021) A nanoscale paper-based near-infrared optical nose (NIRON). Biosens Bioelectron 172: 112763; 10 pages.
Shumeiko et al., (2021) A nanoscale optical biosensor based on peptide encapsulated SWCNTs for detection of acetic acid in the gaseous phase. Sensors and Actuators B: Chemical 327: 128832; 10 pages.
Slor et al., (2021) Judging Enzyme-Responsive Micelles by Their Covers: Direct Comparison of Dendritic Amphiphiles with Different Hydrophilic Blocks. Biomacromolecules 22(3): 1197-1210. With correction.
Slor et al., (2018) Tuning the molecular weight of polymeric amphiphiles as a tool to access micelles with a wide range of enzymatic degradation rates. Chem Commun (Camb) 54(50): 6875-6878.
Whitton and Gillies (2015) Functional aqueous assemblies of linear-dendron hybrids. Journal of Polymer Science Part A: Polymer Chemistry 53(2): 148-172.
Wu et al., (2018) Nanopatterns of Phospholipid Assemblies on Carbon Nanotubes: A Molecular Dynamics Simulation Study. J Phys Chem C 122(13): 7455-7463.
Wulf et al., (2021) Dendron-Polymer Hybrids as Tailorable Responsive Coronae of Single-Walled Carbon Nanotubes. ACS Nano 15(12): 20539-20549. With Supporting Information.
Wulf et al., (2021) Dendron-Polymer Hybrids as Tailorable Coronae of Single-Walled Carbon Nanotube. ChemRxiv. Cambridge: Cambridge Open Engage. Apr. 20, 2021 Version 1; 60 pages. With Supporting Information.
Yaari et al., (2021) A perception-based nanosensor platform to detect cancer biomarkers. Sci Adv 7(47): eabj0852; 11 pages.
Yurekli et al., (2004) Small-angle neutron scattering from surfactant-assisted aqueous dispersions of carbon nanotubes. J Am Chem Soc 126(32): 9902-9903.
Zhang et al., (2013) Molecular recognition using corona phase complexes made of synthetic polymers adsorbed on carbon nanotubes. Nat Nanotechnol 8(12): 959-968.
Zheng (2019) Sorting Carbon Nanotubes. In: Li Y, Maruyama S (eds) Single-Walled Carbon Nanotubes. Topics in Current Chemistry Collections. Springer, Cham. https://doi.org/10.1007/978-3-030-12700-8_5; pp. 129-164.

(56) References Cited

OTHER PUBLICATIONS

Zheng et al., (2020) Dye Quenching of Carbon Nanotube Fluorescence Reveals Structure-Selective Coating Coverage. CS Nano 14(9): 12148-12158.

* cited by examiner

PEG-dendron
-nahthyl -naphthoate -pentyl -hexanoate

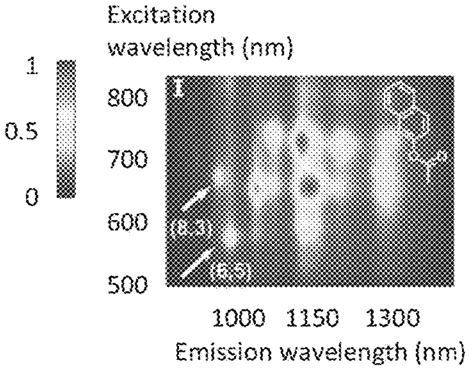
Figure 7A
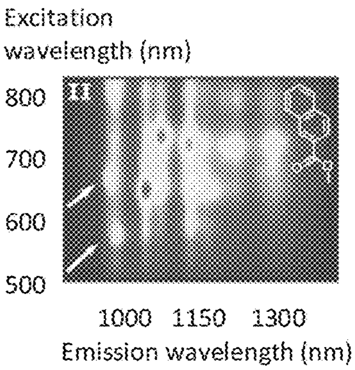
Figure 7B
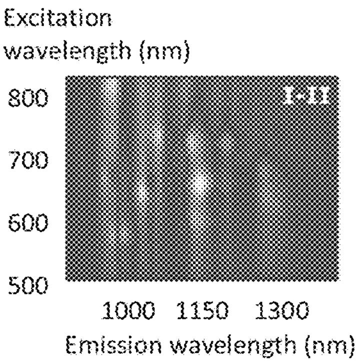
Figure 7C
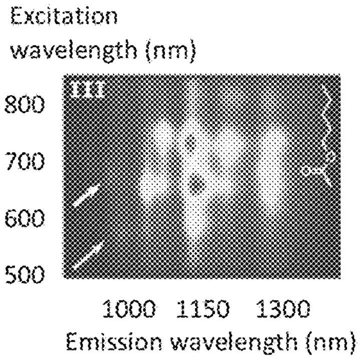
Figure 7D
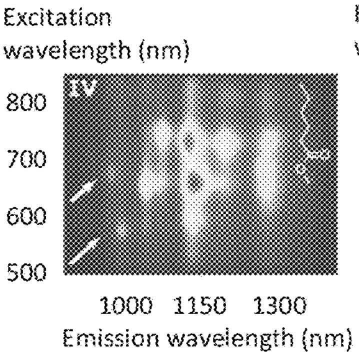
Figure 7E
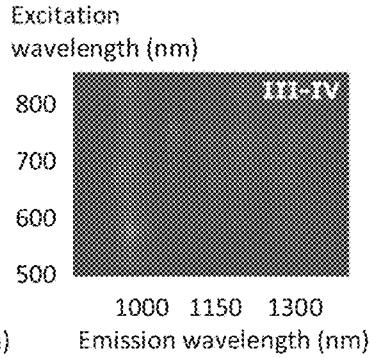
Figure 7F
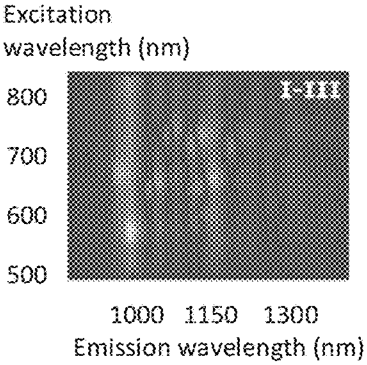
Figure 7G
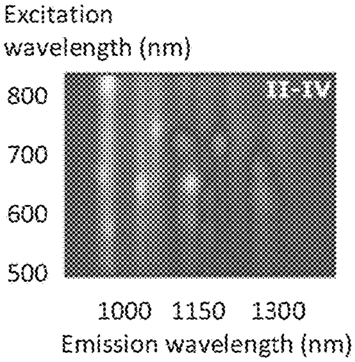
Figure 7H
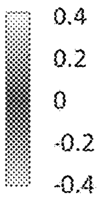

DENDRON-POLYMER HYBRIDS AS TAILORABLE CORONAE OF SINGLE-WALLED CARBON NANOTUBES AND USES THEREOF

FIELD OF INVENTION

The present invention relates to complexes comprising dendron-polymer hybrids and single-walled carbon nanotubes and methods of use thereof as a sensing platform for detecting the presence of a protein, particularly an enzyme.

BACKGROUND

Single-walled carbon nanotubes (SWCNTs) find broad applications as biomedical sensors, mainly due to their intrinsic fluorescence emission in the near-infrared (NIR) transparency window of biological tissues, that allow for in vitro and in vivo sensing of deeper tissues. SWCNTs can be described as graphene sheets in the form of cylinders, resulting in nanotubes with different (n,m)-chiralities, depending on their roll-up vector. The fluorescence emission peak intensities and wavelengths of a SWCNT sample are dependent on the composition of nanotubes with different chiralities and the dielectric environment, and are usually in the range of 900-1,500 nm.

Owing to their graphene-like surface, SWCNTs are highly hydrophobic and require functionalization with dispersants such as low molecular weight surfactants, single-stranded DNA, RNA, suitable proteins, peptides, peptoids, or amphiphilic polymers, in order to form stable colloidal suspensions in aqueous media. The interactions enable the binding of the dispersant to the surface of the SWCNT, primarily through π-π-stacking between the graphene lattice and aromatic groups (DNA, polymers), or hydrophobic interactions (surfactants, phospholipids).

For sensing applications, the dispersing agents typically incorporate a recognition element specific to the analyte to be detected (e.g., aptamers, antibodies, binding peptides). Alternatively, the SWCNTs can be capped with a corona phase, that due to its structure, conformation, and charge is able to selectively bind certain analytes. The dispersants forming the corona phase are very often amphiphilic polymers, that do not suffer from effects like aging or biodegradation compared to aptamers or binding proteins. Each corona phase can influence the fluorescence emission of the SWCNTs, due to its density and/or interactions with the SWCNT surface, Fluorescence emission of a certain chirality can be altered by the distinct dielectric environment that the corona phase induces around the SWCNTs (Hertel et al., Nano Lett. 2005, 5, 511-514). Charge transfer effects from the capping molecules to the SWCNT or vice versa may also occur (Kuang et al., J. Phys. Chem. C 2021, 125, 8125-8136; Papadopoulos et al., Nanoscale 2021, 13, 11544-11551). Upon interaction with a target analyte, changes in the corona phase, for example detaching and/or cleavage of the amphiphiles capping the SWCNTs, occur. These changes alter the dielectric environment of the nanotubes and can be monitored via NIR-fluorescence emission (Gao et al., Chem. Phys. 2013, 413, 35-38; Hartel et al., Nano Lett. 2005, 5, 511-514; Heller et al., PNAS 2011, 108, 8544-8549).

Corona-based recognition was reported for different types of analytes, including small biomolecules and proteins (Zhang et al., Nat. Nanotechnol. 2013, 8, 959-968; Kruss et al., JACS 2014, 136, 713-724; Bisker et al., Nat. Commun. 2016, 7, 10241; Hendler-Neumark et al., Sensors 2019, 19, 5403; Amir et al., Adv. Mater. Interfaces 2021, U.S. Pat. No. 2,101,591; Bisker et al., ACS Sensors 2018, 3, 367-377; Ehrlich et al., Small 2021, 17, 2101660; Pinals et al., Nano Lett. 2021, 21, 2272-2280; Cho et al., Anal. Chem. 2021, 93, 14685-14693; and Zvi, Sci. Adv. 2021, 7, eabj0852). The nature of the exposed, hydrophilic part of the amphiphilic dispersant is important for forming an analyte-specific corona phase. The corona phase is also influenced by its hydrophobic anchoring unit, attached to the SWCNTs. For the recognition of fibrinogen, SWCNTs suspended by a polyethylene glycol (PEG) polymer coupled to a phospholipid with a chain length of 16 carbon atoms were found to have the highest optical response, while coupling to a phospholipid with 14 or 18 carbon atoms showed a significantly weaker response (Bisker et al., Nat. Commun. 2016, 7, 10241). Hence, both the polymer, which is exposed to the solution and thus to the analyte, as well as the hydrophobic anchoring portion of the amphiphile play equally important roles in the formation of a corona phase suitable for sensing applications.

Recently, several approaches have emerged for producing libraries of amphiphilic linear copolymers and block-copolymers that can be used for suspending SWCNTs for specific applications (Gillen et al., Front. Chem. 2019, 7, 1-13). These include combinatorial high-throughput screening of a library of polymers (Zhang et al., Nat. Nanotechnol. 2013, 8, 959-968; Kruss et al., JACS 2014, 136, 713-724; Bisker et al., Nat. Commun. 2016, 7, 10241), high-throughput directed evolution (Lambert et al., Chem. Commun. 2019, 55, 3239-3242; Jeong et al., Sci. Adv. 2019, 5, eaay3771), reversible addition-fragmentation chain transfer polymerization (Dong et al., PNAS 2020, 117, 26616-26625; Lee et al., Adv. Healthc. Mater. 2020, 9, 2000429), and random peptide synthesis (Shumeiko et al., Sensors Actuators, B Chem. 2021, 327, 128832; Shumeiko et al., Biosens. Bioelectron. 2021, 172, 112763). These approaches suffer from challenges resulting from elaborated synthesis, multiple processing steps, or limited control over the final product, and give rise to the need for different approaches for generating a library of highly versatile amphiphilic polymers with a wide range of molecular structures and functions. The future of corona phase sensing applications is thus dependent on the development of additional methods to create libraries of amphiphilic molecules.

U.S. Pat. No. 10,837,045 describes a sensor assembly probe for determining enzymatic activity. The sensor assembly probe includes one or more fluorescent hydrophobic semi-conductive nanoparticles disposed in an aqueous medium. The assembly further includes an amphiphilic polymer including a substrate for a predetermined enzyme. The amphiphilic polymer coats at least a portion of a surface of the fluorescent hydrophobic semi-conductive nanoparticle.

U.S. Pat. No. 9,664,677 describes a complex, where the complex includes a photoluminescent nanostructure and a polymer free from selective binding to an analyte, the polymer adsorbed on the photoluminescent nanostructure, and a selective binding site associated with the complex.

US 2018/0356414 describes corona phase molecular recognition (CoPhMoRe) utilizing a heteropolymer adsorbed onto and templated by a nanoparticle surface to recognize a specific target analyte including proteins. A variant of a CoPhMoRe screening procedure of single walled carbon nanotubes (SWCNTs) can be used against a panel of human blood proteins, revealing a specific corona phase that recognizes fibrinogen and insulin with high selectivity.

WO 2021/240516 describes an optical sensor device for determining the presence of at least one volatile compound (VC) in a gaseous environment, the device comprising a light responsive surface comprising a material-wrapped single walled carbon nanotube (SWCNT), the device being configured and operable for allowing interaction between the at least one VC in the gaseous environment and the SWCNT and/or the material wrapping same; and for emitting NIR photoluminescence indicative of said interaction.

Dendrons are tree-like molecular structures with multiple end-groups, depending on the number of branching points, i.e., the dendron generation, and a focal point that enables coupling, e.g., to a polymer. Dendrons can vary in flexibility, size, and hydrophobicity, providing high degrees of freedom and molecular precision in creating hydrophobic structures. Combining hydrophobic dendrons bearing hydrophobic end-groups with hydrophilic polymers, yields amphiphilic polymer-dendron hybrids. The stability of micellar assemblies of these amphiphilic macromolecules, in particular PEG-dendron and PAA-dendron hybrids, are dependent on the amphiphilic ratio between the polymer tail and the hydrophobic dendron (Whitton et al., J. Polym. Sci. Part A Polym. Chem. 2015, 53, 148-172; Gitsov, J. Polym. Sci. Part A Polym. Chem. 2008, 46, 5295-5314; Harnoy et al., Biomacromol. 2017, 18, 1218-1228; Slor et al., Chem. Commun. 2018, 54, 6875-6878; Slor et al., Biomacromolecules 2021, 22, 1197-1210; Harnoy et al., JACS 2014, 136, 7531-7534; Segal et al., JACS 2017, 139, 803-810).

U.S. Pat. No. 10,869,939 describes a molecular design that allows micelles to report their activation and disassembly by an enzymatic trigger. The molecular design is based on the introduction of a labeling moiety selected from a fluorescent dye, a dark quencher, combinations of dyes or dyes/quenchers, and a fluorinated moiety (a $^{19}F$-magnetic resonance (MR) probe for turn ON/OFF of a $^{19}F$-MR signal) through covalent binding to the focal point of amphiphilic polymer-dendron hybrids with the labeling moiety. At the assembled micellar state, the dyes are closely packed and hence the probability for intermolecular interactions increases significantly, leading to alteration of the fluorescent properties (signal quench or shift) or the $^{19}F$-MR signal (OFF state) of the micelles. Upon enzymatic cleavage of the hydrophobic end-groups from the enzyme-responsive dendron, the polymers become hydrophilic and disassemble. This structural change is then translated into a spectral change as dye-dye interactions are halted and the dyes regain their intrinsic fluorescent properties, or alternatively by turn ON the $^{19}F$-MR signal.

Dendrons can be coupled to a variety of polymers to create a library of amphiphilic molecules with the ability to suspend SWCNTs in aqueous environment and provide designable capping agents to address the requirements of a particular application. By way of example, polystyrene coupled to pyrene-functionalized dendrons suspend SWCNTs in THF (Bahun et al., J. Polym. Sci. Part A Polym. Chem. 2010, 48, 1016-1028), while hydrophilic dendrons coupled to a hydrophobic alkyl-chain or pyrene suspend SWCNTs in water, due to increasing hydrophilicity with increasing dendron generation (Setaro et al., Chem. Phys. Lett. 2010, 493, 147-150; Ernst et al., J. Phys. Chem. C 2013, 117, 1157-1162; Ernst et al., J. Phys. Chem. C 2017, 121, 18887-18891; Gutierrez-Ulloa et al., ChemNanoMat 2018, 4, 220-230).

Maeda et al., (Nanoscale 2018, 10, 23012-23017) describes single-walled carbon nanotubes (SWNTs) that were functionalized by reacting them with sodium naphthalenide and dendrons to control their photoemission in the near-IR region. The functionalized SWNTs were characterized by absorption, Raman, and photoluminescence (PL) spectroscopy. The degree of functionalization of the SWNTs decreased with the increasing bulkiness of the dendrons used. Density functional theory (DFT) calculations of the functionalized SWNTs with dendrons suggest that the adducts with less bulky hydroalkylated substitution are stable in Clar structures and the addition positions predominantly determine the PL peak positions.

Functional composite materials such as fluorescent SWCNTs non-covalently functionalized by synthetic amphiphilic polymers that can change their spectral properties in response to interactions with target analytes have a plethora of applications in fields ranging from sensors to biomedical imaging There is a great unmet need for new amphiphiles with interchangeable building blocks that can form individual coronae around the SWCNTs, and can be tailored for a specific application.

SUMMARY

The present invention relates to enzyme-responsive polymer-dendron amphiphiles that can be used to suspend SWCNTs in aqueous media. These dendritic amphiphiles are composed of a hydrophilic polymer conjugated to a hydrophobic dendron containing hydrophobic end-groups that are enzymatically cleavable. By tailoring the structure of the enzyme-responsive end-groups, dendritic amphiphiles that respond to a specific enzyme are designed. Upon contact with the enzyme, an enzymatically-induced modification of the amphiphiles occurs thereby resulting in a change in the amphiphiles structure that affects the SWCNTs fluorescence properties. Detection of changes in the fluorescence properties of the SWCNTs enables sensing of the presence of the enzyme in a sample. The present invention therefore offers a modular approach to designing SWCNT-based sensors for various enzymes of choice.

Disclosed herein for the first time is the use of molecular hybrids or conjugates that contain a hydrophilic polymer and a hydrophobic dendron containing an enzymatically cleavable site to suspend SWCNTs and form a corona phase capping the surface of the nanotubes. When exposed to the enzyme, changes in the corona phase occur thereby modulating the optical signal obtained from the SWCNTs. By measuring the optical signal induced by the SWCNTs, detection of the enzyme is afforded.

The present invention provides a dendron-polymer hybrid with hydrophobic dendrons containing end-groups capable of adsorbing to the SWCNTs and forming a corona phase wrapping the SWCNTs. These dendron-polymer hybrids are susceptible to structural modifications when in contact with an enzyme due to an enzymatically cleavable site incorporated in the hydrophobic dendrons. When in contact with the enzyme, the structural modifications of the hybrids change the interactions of the amphiphiles with the SWCNTs surface which can subsequently be directly related to differences in the intrinsic near-infrared fluorescence emission of the various chiralities in the SWCNTs.

According to a first aspect, there is provided a complex comprising a hybrid polymer comprising a hydrophilic polymer covalently bound to a hydrophobic dendron, the dendron comprising at least one enzymatically cleavable hydrophobic end-group, and a single-walled carbon nanotube, wherein the hybrid polymer is non-covalently attached to the surface of the single-walled carbon nanotube through the at least one enzymatically cleavable hydrophobic end-group to form a corona phase capping the nanotube.

In one embodiments, the hydrophilic polymer comprises polyethylene glycol (PEG), polyacrylic acid (PAA), poly (hydroxyethyl acrylate), poly(oligo-ethylene glycol acrylate), polyacrylamide, hydrophilic polymethacrylate, polymethyl oxazoline, polyethyl oxazoline, polysarcosine, polypeptide, polypeptoid, polyamine, hydrophilic nylon, polyvinyl alcohol, hydrophilic protein, or polycarbohydrate. Each possibility represents a separate embodiment. In some embodiments, the hydrophilic polymer comprises polyethylene glycol (PEG), polyacrylic acid (PAA), poly(2-hydroxyethyl acrylate), or poly(oligo-ethylene glycol acrylate). Each possibility represents a separate embodiment. In one embodiment, the hydrophilic polymer comprises polyethylene glycol (PEG). In another embodiment, the hydrophilic polymer comprises polyacrylic acid (PAA). In other embodiments, the hydrophilic polymer has a molecular weight of about 0.5 to about 70 kDa, including each value within the specified range. In yet other embodiments, the hydrophilic polymer has a molecular weight of about 0.5 to about 50 kDa, including each value within the specified range. In particular embodiments, the hydrophilic polymer has a molecular weight of about 0.5 to about 20 kDa, including each value within the specified range.

In further embodiments, the hydrophilic polymer is covalently bound to the hydrophobic dendron by a group selected from the group consisting of —Z—, —$X^1$—Z—$X^2$—, —$Z^1$—$X^1$—$Z^2$—$X^2$—, wherein Z, Z', and $Z^2$ are each independently selected from $C_1$-$C_{10}$ alkylene, $C_2$-$C_{10}$ alkenylene, $C_2$-$C_{10}$ alkynylene, and arylene; $X^1$ and $X^2$ are each independently selected from —O—; —S—; —NH—; —C(═O)—; —C(═O)—O—; —O—C(═O)—O—; —C(═O)—NH—; —NH—C(═O)—NH—; —NH—C(═O)—O—; —S(═O)—; —S(═O)—O—; —PO(═O)—O—; triazolylene, and any combination thereof. Each possibility represents a separate embodiment.

In some embodiments, the hydrophobic dendron comprises between 0 to 5 generations. In other embodiments, the hydrophobic dendron comprises between 0 to 3 generations. In further embodiments, the hydrophobic dendron is a generation 0 (G0) dendron. In other embodiments, the hydrophobic dendron is a generation 1 (G1) dendron. In yet other embodiments, the hydrophobic dendron is a generation 2 (G2) dendron. In further embodiments, the hydrophobic dendron is a generation 3 (G3) dendron.

In certain embodiments, each generation of the hydrophobic dendron comprises a linear or branched $C_1$-$C_{20}$ alkylene, $C_2$-$C_{20}$ alkenylene, $C_2$-$C_{20}$ alkynylene or arylene moiety which is substituted at each end with a group selected from the group consisting of —O—, —S—, —NH—, —C(═O)—, —C(═O)—O—, —O—C(═O)—O—, —C(═O)—NH—, —NH—C(═O)—NH—, —NH—C(═O)—O—, —S(═O)—, —S(═O)—O—, —PO(═O)—O—, and any combination thereof. Each possibility represents a separate embodiment.

In various embodiments, each generation of the dendron is derived from a compound having the following structure HX—Z—XH or HX—Z—$CO_2H$, wherein X is independently at each occurrence NH, S or O, and Z is selected from the group consisting of $C_1$-$C_{10}$ alkylene, $C_2$-$C_{10}$ alkenylene, $C_2$-$C_{10}$ alkynylene, and arylene. Each possibility represents a separate embodiment. In other embodiments, each generation of the dendron is derived from a compound selected from the group consisting of HX—$CH_2$—$CH_2$—XH, HX—$(CH_2)_{1-3}$—$CO_2H$, and HX—$CH_2$—CH(XH)—$CH_2$—XH wherein X is independently at each occurrence NH, S or O. Each possibility represents a separate embodiment. In particular embodiments, each generation of the dendron is derived from a compound selected from the group consisting of HS—$CH_2$—$CH_2$—OH, HS—$(CH_2)_{1-3}$—$CO_2H$ and HS—$CH_2$—CH(OH)—$CH_2$—OH. Each possibility represents a separate embodiment.

In some embodiment, each generation of the dendron comprises a branching unit capable of connecting between dendron generations. In specific embodiments, the branching unit is a hydrophobic branching unit. In particular embodiments, the hydrophobic branching unit is an arylene, for example a $C_6$-arylene, which is substituted with one or more of —O—, —S—, —NH—, —C(═O)—, —C(═O)—O—, —O—C(═O)—O—, —C(═O)—NH—, —NH—C(═O)—NH—, —NH—C(═O)—O—, —S(═O)—, —S(═O)—O—, —PO(═O)—O—, and any combination thereof. Each possibility represents a separate embodiment.

According to the principles of the present invention, the dendron comprises at least one enzymatically cleavable hydrophobic end-group. In some embodiments, the hydrophobic end-groups are aromatic end-groups. In other embodiments, the hydrophobic end-groups are aliphatic end-groups. In yet other embodiments, the hydrophobic end-groups are covalently attached to the dendrons through an enzymatically cleavable functional moiety. In particular embodiments, the hydrophobic end-groups are selected from the group consisting of a naphthyl group, a naphthoate group, a phenylacetamide group, a pentyl group, a hexyl group, a heptyl group, an octyl group, a nonyl group, a decyl group, a pentanoate group, a hexanoate group, a heptanoate group, an octanoate group, a nonanoate group, a decanoate group, and a phenylacetamide group. Each possibility represents a separate embodiment. In other particular embodiments, the hydrophobic end-groups are selected from the group consisting of a naphthyl group, a naphthoate group, a pentyl group, a hexanoate group, an octanoate group, and a phenylacetamide group. Each possibility represents a separate embodiment.

In additional embodiments, the enzymatically cleavable functional moiety is selected from the group consisting of an ester, an amide, a carbamate, a carbonate, a urea, a sulfate, an amidine, an ether, a phosphate, a phosphoamide, a sulfamate, a nitro, an azo, and a trithionate. Each possibility represents a separate embodiment. In specific embodiments, the enzymatically cleavable functional moiety is represented by the structure of —O—C(O)—R', —C(O)—OR'—NH—C(O)—R' or —C(O)—NHR' wherein R' is $C_1$-$C_{12}$ alkyl or an aryl. Each possibility represents a separate embodiment.

In certain embodiments, the enzymatically cleavable functional moiety is cleavable by an amidase. In other embodiments, the enzymatically cleavable functional moiety is cleavable by an esterase. In yet other embodiments, the enzymatically cleavable functional moiety is cleavable by a urease.

Currently preferred polymer hybrids in accordance with the principles of the present invention are represented by the structures depicted in FIGS. 1B, 14A, 16A, and 16B. Each possibility represents a separate embodiment.

In various embodiments, the single-walled carbon nanotubes have diameters ranging from about 0.6 nanometer (nm) to about 100 nanometers (nm), including each value within the specified range. In other embodiments, the single-walled carbon nanotubes have diameters ranging from about 0.7 nm to about 50 nm, including each value within the specified range. According to yet other embodiments, the single-walled carbon nanotubes have diameters ranging from about 0.8 nm to about 10 nm, including each value within the specified range.

In some embodiments, the single-walled carbon nanotubes have lengths ranging from about 50 nanometers (nm)

to about 10 millimeters (mm), including each value within the specified range. In other embodiments, the single-walled carbon nanotubes have lengths ranging from about 250 nm to about 1 mm, including each value within the specified range. In yet other embodiments, the single-walled carbon nanotubes have lengths ranging from about 0.5 micrometer (μm) to about 100 micrometers (μm), including each value within the specified range.

In certain embodiments, the molar ratio between the hybrid polymer and the single-walled carbon nanotube ranges from about $10^6$:1 to about 100:1, including all iterations of ratios within the specified range. In other embodiments, the molar ratio between the hybrid polymer and the single-walled carbon nanotube ranges from about $10^5$:1 to about $10^3$:1, including all iterations of ratios within the specified range.

According to another aspect, the present invention provides a method of detecting the presence of an enzyme in a sample, the method comprising the steps of:

(i) providing a complex comprising a hybrid polymer comprising a hydrophilic polymer covalently bound to a hydrophobic dendron, the dendron comprising at least one enzymatically cleavable hydrophobic end-group, and a single-walled carbon nanotube, wherein the hybrid polymer is non-covalently attached to the surface of the single-walled carbon nanotube through the at least one enzymatically cleavable hydrophobic end-group to form a corona phase capping the nanotube;

(ii) exposing the complex to the sample; and (iii) measuring an optical property of the complex prior to and following step (ii), whereby a change in the optical property of the complex following step (ii) as compared to the optical property prior to step (ii) is indicative of the presence of the enzyme in the sample.

In various embodiments, the optical property comprises a fluorescence signal. In other embodiments, the change in the optical property comprises a decay in the fluorescence intensity. In yet other embodiments, the change in the optical property comprises a decay in the fluorescence intensity in near-infrared wavelengths. In further embodiments, the change in the optical property comprises a change in the near-infrared fluorescence emission of the chiralities in the SWCNTs.

In certain embodiments, detecting the presence of an enzyme in a sample comprises measuring enzymatic activity. In other embodiments, detecting the presence of an enzyme in a sample comprises monitoring enzymatic activity. In yet other embodiments, detecting the presence of an enzyme in a sample comprises identifying the presence of a pathogen excreting an enzyme in the sample.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1A shows a schematic representation of the amphiphilic polymer-dendron hybrid which contains a hydrophilic polymer chain, and a hydrophobic dendron that bears hydrophobic end-groups. FIG. 1B shows the chemical structure of an amphiphilic polymer-dendron hybrid which contains polyethylene glycol (PEG) serving as the hydrophilic chain, coupled to a dendron bearing naphthyl, naphthoate, pentyl or hexanoate hydrophobic end-groups. FIG. 1C shows a schematic representation of the functionalization of SWCNTs with the polymer-dendron amphiphiles (SWCNT@PEG-dendrons) which was performed via surfactant exchange (dialysis) of sodium cholate suspended SWCNTs (SWCNT@SC). FIG. 1D shows the absorption spectrum of SWCNT@PEG-D-pentyl (solid line) compared to the absorption spectrum of SWCNT@SC (dashed line) prior to functionalization.

FIG. 2A shows SWCNT@PEG-D-naphthyl and PEG-D-naphthyl. FIG. 2B shows SWCNT@PEG-D-naphthoate and PEG-D-naphthoate. FIG. 2C shows SWCNT@PEG-D-pentyl and PEG-D-pentyl. FIG. 2D shows SWCNT@PEG-D-hexanoate and PEG-D-hexanoate.

FIG. 3A shows the chemical structure of a PEG-dendron hybrid bearing carboxylic end-groups (PEG-D-COOH). FIG. 3B shows aggregation of sodium cholate suspended carbon nanotubes upon removal of sodium cholate during dialysis in the presence of PEG-D-COOH.

FIGS. 4A-4D show NIR-absorption spectra of SWCNTs before (SWCNT@SC; dashed lines) and after (solid lines) surfactant exchange to: FIG. 4A SWCNT@PEG-D-naphthyl; FIG. 4B SWCNT@PEG-D-naphthoate; FIG. 4C SWCNT@PEG-D-pentyl; and FIG. 4D SWCNT@PEG-D-hexanoate.

FIGS. 5A-5D show NIR-fluorescence spectra of SWCNTs before (SWCNT@SC; dashed lines) and after (solid lines) surfactant exchange to: FIG. 5A SWCNT@PEG-D-naphthyl; FIG. 5B SWCNT@PEG-D-naphthoate; FIG. 5C SWCNT@PEG-D-pentyl; and FIG. 5D SWCNT@PEG-D-hexanoate at an excitation wavelength of $\lambda_{ex}$=730 nm.

FIGS. 6A and 6B show the fluorescence intensity and normalized fluorescence intensity, respectively, of the different SWCNT@PEG-dendrons at an excitation wavelength of $\lambda_{ex}$=730 nm. FIG. 6C shows the normalized absorption of the SWCNT@PEG-dendrons. FIG. 6D shows the normalized fluorescence spectra of the SWCNT@PEG-dendrons following the addition of SDBS.

FIGS. 7A-7L show the fluorescence emission of SWCNT@PEG-dendrons. FIGS. 7A, 7B, 7D, and 7E show normalized fluorescence excitation-emission spectra for SWCNT@PEG-D-naphthyl, SWCNT@PEG-D-naphthoate, SWCNT@PEG-D-pentyl, and SWCNT@PEG-D-hexanoate, respectively. Arrows mark the fluorescence emission of the (6,5) and the (8,3) chiralities. FIG. 7C shows differences between the two SWCNT@PEG-dendron samples with aromatic polymer-dendrons, and FIG. 7F shows differences between the two SWCNT@PEG-dendron samples with aliphatic polymer-dendrons. FIGS. 7G and 7H show differences between the two SWCNT@PEG-dendron samples with their ester group in the same orientation. FIGS. 7I-7L show normalized fluorescence emission before (solid lines) and after (dashed lines) the addition of 0.2% (w/v) SDBS to suspensions of SWCNT@PEG-D-naphthyl (7I), SWCNT@PEG-D-naphthoate (7J), SWCNT@PEG-D-pentyl (7K), and SWCNT@PEG-D-hexanoate (7L).

FIG. 8A shows a schematic representation of the cleavage of the PEG-dendrons by PLE.

FIG. 8H-81 show the fluorescence response of SWCNT@PEG-D-hexanoate. FIGS. 8J-8Q show the quantification of the degradation process of PEG-dendrons wrapping SWCNTs (solid lines) and as free micellar assemblies (dashed lines) after separation via HPLC. FIGS. 8J, 8L, 8N, and 8P show degradation of the intact polymer bearing all four end-groups and FIGS. 8K, 8M, 8O, and 8Q show quantification of the concentration of the cleaved-off end-groups. FIGS. 8J-8K—naphthol; FIGS. 8L-8M—naphthoic acid; FIGS. 8N-8O—pentyl; and FIGS. 8P-8Q—hexanoate.

FIG. 9A shows the absorption spectrum of SWCNT@PEG-D-naphthyl before (t=0 h) and after incubation with PLE for 24 h (t=24 h). FIG. 9B shows the fluorescence spectrum of SWCNT@PEG-D-naphthyl before (t=0 h) and after (t=24 h) the incubation with PLE.

FIGS. 10A and 10B show the fluorescence spectra after incubation of PEG-D-naphthyl with PLE and BSA, respectively, compared to their control in PBS buffer. FIGS. 10C and 10D show the fluorescence spectra after incubation of PEG-D-naphthoate with PLE and BSA, respectively, compared to their control in PBS buffer.

FIGS. 10E and 10F show the fluorescence spectra after incubation of PEG-D-pentyl with PLE and BSA, respectively, compared to their control in PBS buffer. FIGS. 10G and 10H show the fluorescence spectra after incubation of PEG-D-hexanoate with PLE and BSA, respectively, compared to their control in PBS buffer.

FIG. 11A corresponds to SWCNT@PEG-D-naphthyl; FIG. 11B corresponds to SWCNT@PEG-D-naphthoate; FIG. 11C corresponds to SWCNT@PEG-D-pentyl; and FIG. 11D corresponds to SWCNT@PEG-D-hexanoate.

FIGS. 12A, 12B, 12C, and 12D show the correlation of the time-dependent fluorescence signal of SWCNT@PEG-D-naphthyl, SWCNT@PEG-D-naphthoate, SWCNT@PEG-D-pentyl, and SWCNT@PEG-D-hexanoate, respectively, with the concentration increase of the cleaved-off end-groups as determined via HPLC. FIG. 12E shows a schematic representation of the proposed equilibrium dependent degradation mechanism which is dependent on the interaction between SWCNT/PEG-dendron assemblies.

FIG. 13A shows the normalized absorption spectra of SWCNT@SC (dashed line) before dialysis and SWCNT@PLE (solid line) after dialysis with PLE. FIG. 13B shows that SWCNTs are not suspended after tip-sonication with hexanoic acid.

FIG. 14A shows the chemical structure of an amphiphilic PEG-dendron hybrid which contains a phenylacetamide end-group. FIG. 14B shows a schematic representation of the cleavage of the PEG-D-amide by PGA. FIG. 14C shows the normalized fluorescence excitation-emission spectra for SWCNT@PEG-D-amide having similar fluorescence emission to the aliphatic SWCNT@PEG-dendrons. FIG. 14D shows the wavelength shift of the (10,2) chirality upon the addition of SDBS to a SWCNT. FIG. 14E shows the correlation of the time dependent fluorescence signal of SWCNT@PEG-D-amide to the generation of the cleaved polymer, measured after separation via HPLC upon addition of PGA.

FIG. 16A PAA-D-octanoate. FIG. 16B PEG-D-octanoate.

FIGS. 17A-17D show SWCNT@PEG-D-octanoate before (t=0 h) and after (t=12 h) incubation with PLE for 12 hours at different concentrations: FIG. 17A 0 μM, FIG. 17B 0.2 μM, FIG. 17C 0.75 μM, and FIG. 17D 1.5 μM. FIGS. 17E-17H show SWCNT@PAA-D-octanoate before (t=0 h) and after (t=12 h) incubation with PLE for 12 hours at different concentrations: FIG. 17E 0 μM, FIG. 17F 0.2 μM, FIG. 17G 0.75 μM, and FIG. 17H 1.5 μM.

FIG. 18A SWCNT@PAA-D-octanoate in PBS (asterisks), 0.2 μM PLE (triangles), 0.75 μM PLE (circles), and 1.5 μM (diamonds). FIG. 18B SWCNT@PEG-D-octanoate in PBS (asterisks), 0.2 μM PLE (triangles), 0.75 μM PLE (circles), and 1.5 μM (diamonds).

DETAILED DESCRIPTION

Figure 1A:
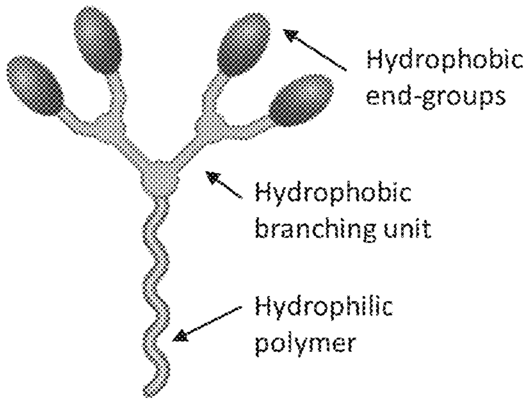
FIGS. 1A-1D show polymer-dendron hybrids as modular amphiphilic macromolecules capable of dispersing SWCNTs.

The present invention provides dendron-polymer hybrids capable of dispersing SWCNTs in aqueous media. The present invention further provides the use of a complex comprising the dendron-polymer hybrids and SWCNTs as a sensing platform for detecting the presence of enzymes.

Disclosed herein for the first time is a family of amphiphilic hybrids comprising a hydrophilic polymer covalently linked to a hydrophobic dendron that are capable of dispersing SWCNTs in water through direct non-covalent interactions between the dendron's hydrophobic end-groups and the graphene lattice of the SWCNTs. Introducing an enzymatically cleavable site into the hydrophobic dendrons enables the use of the hybrids-SWCNTs complexes as sensing platforms for detecting the presence of the enzyme in a sample.

The inventors of the present invention have designed PEG/PAA-dendrons having aliphatic or aromatic hydrophobic end-groups that form a corona on the surface of SWCNTs by non-covalent hydrophobic interactions. The hydrophobic end-groups were attached to the dendrons through ester or amide functional moieties. The hybrids containing aliphatic end-groups attached through an ester moiety, showed similar fluorescence emission, similar accessible surface area, as well as similar stability and reactivity towards an activating enzyme. However, due to the ester group acting either as an electron acceptor or an electron donor towards the naphthalene π-system of the SWCNTs, significant differences in fluorescence modulation between the end-groups, including fluorescence emission intensity and wavelength, were observed. Upon enzymatic degradation of the hybrids by esterase as a model, the enzymatic cleavage of the end-groups induced a spectral response of the SWCNTs. It was also shown that the accessible surface area on the SWCNTs can be correlated with the ability of the hybrids-SWCNTs complexes to show spectral responses induced by the activating enzyme. The amphiphile-SWCNTs complex containing an amide functional moiety for attaching the hydrophobic end-groups of the dendrons was able to successfully monitor amidase activity through the fluorescence signal of the SWCNTs. Furthermore, criteria of the SWCNT sensors (fluorescence modulation and surface accessibility) that enable to monitor the complete enzymatic end-group cleavage were identified.

The present invention thus provides tailorable amphiphilic polymer-dendron hybrids that are synthesized with high molecular precision and overall yields (ca. 90%), whose structure and composition can be tuned by changing the hydrophobic end-groups, branching unit, and hydrophilic polymer. These versatile polymer-dendron structures can be used for designing modular enzyme-responsive NIR-fluorescent SWCNTs as the dendron can be tailored to have branches with varying flexibility and generation number, resulting in different numbers of end-groups and interaction sites on the SWCNT surface. Furthermore, the polymer chain can be varied in charge, flexibility, conductivity, or be designed to attach additional recognition elements or functional groups. This platform of configurable functional composite nanomaterials can be used for numerous applications, for example in studying the stability, reactivity, and susceptibility to enzymatic activity. In addition, monitoring of enzymatic binding in real-time through the transient modulation of the fluorescence emission in the NIR is afforded. Optical sensors emitting light in the NIR can be more easily implemented in vivo thus enabling the use of the complexes for clinical diagnostics.

According to the principles of the present invention, polymer-dendron hybrids useful as modular amphiphilic agents for the suspension of SWCNTs in aqueous media are provided. The polymer-dendron hybrids are amphiphilic macromolecules containing three structural elements (FIG. 1A): I) a linear polymer chain serving as the hydrophilic block, whose hydrophilicity and flexibility depends on its chemical composition and length, II) a hydrophobic dendron body acting as part of the hydrophobic block, whose size, flexibility and hydrophobicity are determined by the chemical structure of the branching units and the dendron's generation, and III) a plurality of hydrophobic end-groups that are covalently attached to the dendron and whose number depends on the generation of the dendron. The advantage of using dendrons as the hydrophobic block capping the SWCNTs in comparison to other architectures such as linear polymers or even branched polymers, is the structural symmetry of the dendritic end-groups as well as their high spatial availability as being present at the termini of the dendritic branches to interact with the surface of the SWCNTs.

The present invention provides polymer-dendron amphiphiles comprising hydrophobic dendritic end-groups that form a corona phase which surrounds and wraps the SWCNTs through non-covalent interactions. The present invention also provides use of the polymer-dendron-SWCNTs complexes for detecting enzymatic activity through changes in the optical properties of the SWCNTs.

In some aspects and embodiments, the present invention relates to PEG-dendron amphiphiles with end-groups that can differ in their interactions with the carbon nanotube surface. The synthetic pathway provides high modularity and simplicity and allows for analysis of the influence of precise changes in the chemical structure of the end-groups on the fluorescence emission of the SWCNTs. The present invention further relates to a method for understanding and exploiting the nature of specific interactions between the anchoring end-groups and the SWCNTs surface. In some aspects and embodiments, ester bonds between the hydrophobic end-groups and the dendron demonstrate the response of the SWCNTs to esterase as a model enzyme. In other aspects and embodiments, amide bonds between the hydrophobic end-groups and the dendron demonstrate the response of the SWCNTs to amidase as a model enzyme. The reactivity of the PEG-dendrons corona of the SWCNTs towards a variety of enzymes can be monitored via fluorescence spectroscopy in the NIR spectral region thereby forming a sensing platform for the detection of enzymatic activity.

According to the principles of the present invention, provided herein is a dendron-polymer hybrid capable of dispersing SWCNTs comprising a hydrophilic polymer chain; and a hydrophobic block comprising a dendron covalently bound to at least one enzymatically cleavable hydrophobic end-group.

Suitable hydrophilic polymers within the scope of the present invention include, but are not limited to, polyethylene glycol (PEG), polyacrylic acid (PAA), poly(2-hydroxyethyl acrylate), and poly(oligo-ethylene glycol acrylate). Each possibility represents a separate embodiment. Additional hydrophilic polymers include, but are not limited to, polyacrylamides, polymethyl oxazoline, polyethyl oxazoline, polysarcosine, polypeptides, polypeptoids, hydrophilic polymethacrylates, polyamines, hydrophilic nylons, polyvinyl alcohol, hydrophilic proteins and polycarbohydrates. Each possibility represents a separate embodiment. In particular embodiments, the hydrophilic polymer has a molecular weight of about 0.5 to about 70 kDa, including each value within the specified range. In one embodiment, the hydrophilic polymer does not contain a protein, a peptide, a polypeptide or a polynucleotide.

The hydrophilic polymer is chemically bound to the hydrophobic dendron. Typical groups in said chemical bonds include, but are not limited to, —Z—, —$X^1$—Z—$X^2$—, —$Z^1$—$X^1$—$Z^2$—$X^2$—, wherein Z, Z', and $Z^2$ are each independently selected from $C_1$-$C_{10}$ alkylene, $C_2$-$C_{10}$ alkenylene, $C_2$-$C_{10}$ alkynylene, and arylene; $X^1$ and $X^2$ are each independently selected from —O—; —S—; —NH—; —C(═O)—; —C(═O)—O—; —O—C(═O)—O—; —C(═O)—NH—; —NH—C(═O)—NH—; —NH—C(═O)—O—; —S(═O)—; —S(═O)—O—; —PO(═O)—O—; triazolylene, and any combination thereof. Each possibility represents a separate embodiment.

The term "dendron" as used herein refers to a hyperbranched monodisperse organic molecule defined by a tree-like or generational structure. In general, dendrons possess three distinguishing architectural features: a branching moiety; an interior area containing generations with radial connectivity to the branching moiety; and a surface region (peripheral region) of terminal moieties. According to the principles of the present invention, the terminal moieties are terminal hydrophobic end-groups comprising enzymatically cleavable sites.

According to certain embodiments, each generation of the hydrophobic dendron comprises a linear or branched $C_1$-$C_{20}$ alkylene, $C_2$-$C_{20}$ alkenylene, $C_2$-$C_{20}$ alkynylene or arylene moiety which is substituted at each end with a group selected from the group consisting of —O—, —S—, —NH—, —C(═O)—, —C(═O)—O—, —O—C(═O)—O—, —C(═O)—NH—, —NH—C(═O)—NH—, —NH—C(═O)—O—, —S(═O)—, —S(═O)—O—, —PO(═O)—O—, and any combination thereof. Each possibility represents a separate embodiment.

In certain aspects and embodiments, each generation is derived from a compound having a structure represented by the formulae HX—Z—XH or HX—Z—$CO_2$H, wherein X is independently at each occurrence NH, S or O, and Z is selected from $C_1$-$C_{10}$ alkylene, $C_2$-$C_{10}$ alkenylene, $C_2$-$C_{10}$ alkynylene, and arylene. Each possibility represents a separate embodiment. According to other embodiments, each generation of the dendron is derived from a compound selected from the group consisting of HX—$CH_2$—$CH_2$—XH, HX—$(CH_2)_{1-3}$—$CO_2$H, and HX—$CH_2$—CH(XH)—$CH_2$—XH wherein X is independently at each occurrence NH, S or O. Each possibility represents a separate embodiment. In one embodiment, each generation of the dendron is derived from a compound selected from the group consisting of HS—$CH_2$—$CH_2$—OH, HS—$(CH_2)_{1-3}$—$CO_2$H and HS—$CH_2$—CH(OH)—$CH_2$—OH. Each possibility represents a separate embodiment.

The hydrophobic dendron of the present invention comprises a preferred number of generations in the range of 0 to 5, more preferably 0 to 3, including each integer within the specified ranges. In one embodiment, the hydrophobic dendron is a generation 0 (G0) dendron. In another embodiment, the hydrophobic dendron is a generation 1 (G1) dendron. In yet another embodiment, the hydrophobic dendron is a generation 2 (G2) dendron. In other embodiments, the hydrophobic dendron is a generation 3 (G3) dendron.

In various embodiments, the dendron comprises a repeating unit selected from the group consisting of:

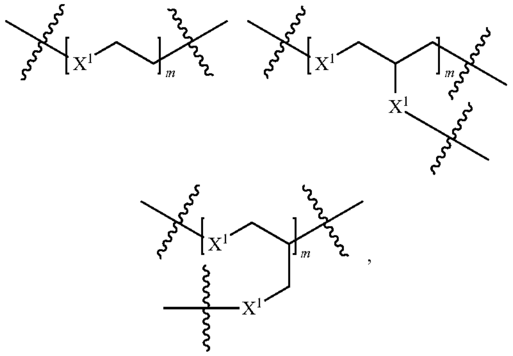

wherein $X^1$ is independently, at each occurrence, selected from the group consisting of O, S and NH; and m is an integer from 1 to 15, including each integer within the specified range.

According to the principles of the present invention, hydrophobic dendrons comprise a branching unit or a plurality of such units that form a part of the first generation, and/or connect between dendron generations. In one embodiment, the branching unit is selected from a group consisting of a substituted or unsubstituted acyclic, cyclic or aromatic hydrocarbon moiety, heterocyclic moiety, a heteroaromatic moiety or any combination thereof. Each possibility represents a separate embodiment. Suitable branching units within the scope of the present invention include, but are not limited to, arylenes (e.g., phenylene), which may be substituted with one or more hydroxyls (e.g., phenols), trimethylolpropane, glycerine, pentaerythritol, polyhydroxy phenols such as phloroglucinol, propylene glycol, tri-substituted alkylamines, diethylenetriamine, triethylenetetramine, diethanolamine, triethanolamine, amino carboxylic acids, such as ethylenediaminetetraacetic (EDTA) and porphyrin, ethylene glycol, ethylenediamine di-substituted alkylamines, diethylenetriamine, triethylenetetramine, diethanolamine, fumaric, maleic, phthalic, malic acid, 6-aminohexanol, 6-mercaptohexanol, 10-hydroxydecanoic acid, 1,6-hexanediol, β-alanine, 2-aminoethanol, 2-aminoethanethiol, 5-aminopentanoic acid, and 6-aminohexanoic acid among others. Each possibility represents a separate embodiment. In one currently preferred embodiment, the branching unit is an unsubstituted or substituted arylene or phenol which may be positioned between the hydrophilic polymer and the first generation of the dendron or may form a part of the first generation, or alternatively may be positioned at one or more intermediary generations of the dendron. Each possibility represents a separate embodiment. The branching unit may further provide additional functionality to the polymer hybrid. According to various embodiments, each of the branching units may be connected to the hydrophilic polymer or to other dendron generations through a functional group selected from the group consisting of —O—, —S—, —NH—, —C(═O)—, —C(═O)—O—, —OC(═O)—O—, —C(═O)—NH—, —NH—C(═O)—NH—, —NH—C(═O)—O—, —S(═O)—, —S(═O)—O—, —PO(═O)—O—, —C═C—, —C≡C—, —$(CH_2)_t$—, wherein t is an integer from 1 to 10, and any combination thereof. Each possibility represents a separate embodiment.

According to the principles of the present invention, the dendrons comprise at least one enzymatically cleavable hydrophobic end-group, typically a plurality of end-groups at the termini of each of the dendron branches. In some embodiments, the hydrophobic end groups are conjugated to the dendron through a functional moiety represented by the structure:

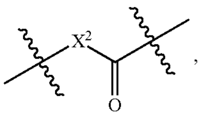

wherein $X^2$ is a part of the terminal repeating unit of said dendron and C(═O) is part of hydrophobic end group; or wherein $X^2$ is part of the hydrophobic end group and C(═O) is a part of the terminal repeating unit of said dendron, or wherein $X^2$—C(═O) is part of the hydrophobic end group, or wherein $X^2$—C(═O) is part of the terminal repeating unit of said dendron; and wherein $X^2$ has the same meaning as $X^1$ defined herein above.

According to the principles of the present invention, the enzymatically cleavable hydrophobic end-group comprises at least one enzymatically cleavable site. An "enzymatically cleavable site" as used herein refers to a region of a compound that is chemically cleaved in the presence of one or more enzymes. In some embodiments, an "enzymatically cleavable site" refers to a region of a compound that is totally or partially cleaved by one or more enzymes. Enzymatically cleavable sites typically include a functional group such as, but not limited to, an ester, an amide, a carbamate, a carbonate, a urea, a sulfate, an amidine, an ether, a phosphate, a phosphoamide, a sulfamate, a nitro, an azo, and a trithionate. Each possibility represents a separate embodiment. Functional groups that can be cleaved by enzymes include, for example —O—C(O)—R', —C(O)—OR'—NH—C(O)—R' or —C(O)—NHR' wherein R' is $C_1$-$C_{12}$ alkyl or an aryl. Each possibility represents a separate embodiment.

It will be appreciated to one skilled in the art that an amide bond is enzymatically cleavable by an amidase. Suitable amidases that can cleave an amide bond include, but are not limited to, aryl-acylamidase, aminoacylase, alkylamidase, and phthalyl amidase. Each possibility represents a separate embodiment. Where an ester bond is present in the hydrophobic dendron termini, it can be cleaved by an esterase. Suitable esterases that can cleave an ester bond include, but are not limited to, carboxylesterase, arylesterase, and acetylesterase. Each possibility represents a separate embodiment. Where the hydrophobic termini contain a urea bond, it can be cleaved by a urease.

The enzymatically cleavable hydrophobic end groups may be present only at the terminal repeating units of the hydrophobic dendron (i.e., the enzymatically cleavable hydrophobic end group is not present in intermediary generations of the dendron) or it may be present in the end-groups in addition to its presence at the intermediary generations of the dendron. Each possibility represents a separate embodiment.

Within the scope of the present invention are hydrophobic end-groups that include, but are not limited to a naphthyl group, a naphthoate group, a phenylacetamide group, a pentyl group, a hexyl group, a heptyl group, an octyl group, a nonyl group, a decyl group, a pentanoate group, a hexanoate group, a heptanoate group, an octanoate group, a nonanoate group, a decanoate group, and a phenylacetamide group. Each possibility represents a separate embodiment. Exemplary hydrophobic end-groups include, but are not limited to, a naphthyl group, a naphthoate group, a pentyl group, a hexanoate group, an octanoate group, and a phenylacetamide group. Each possibility represents a separate embodiment.

Currently preferred dendritic hybrids include those represented by the following structure:

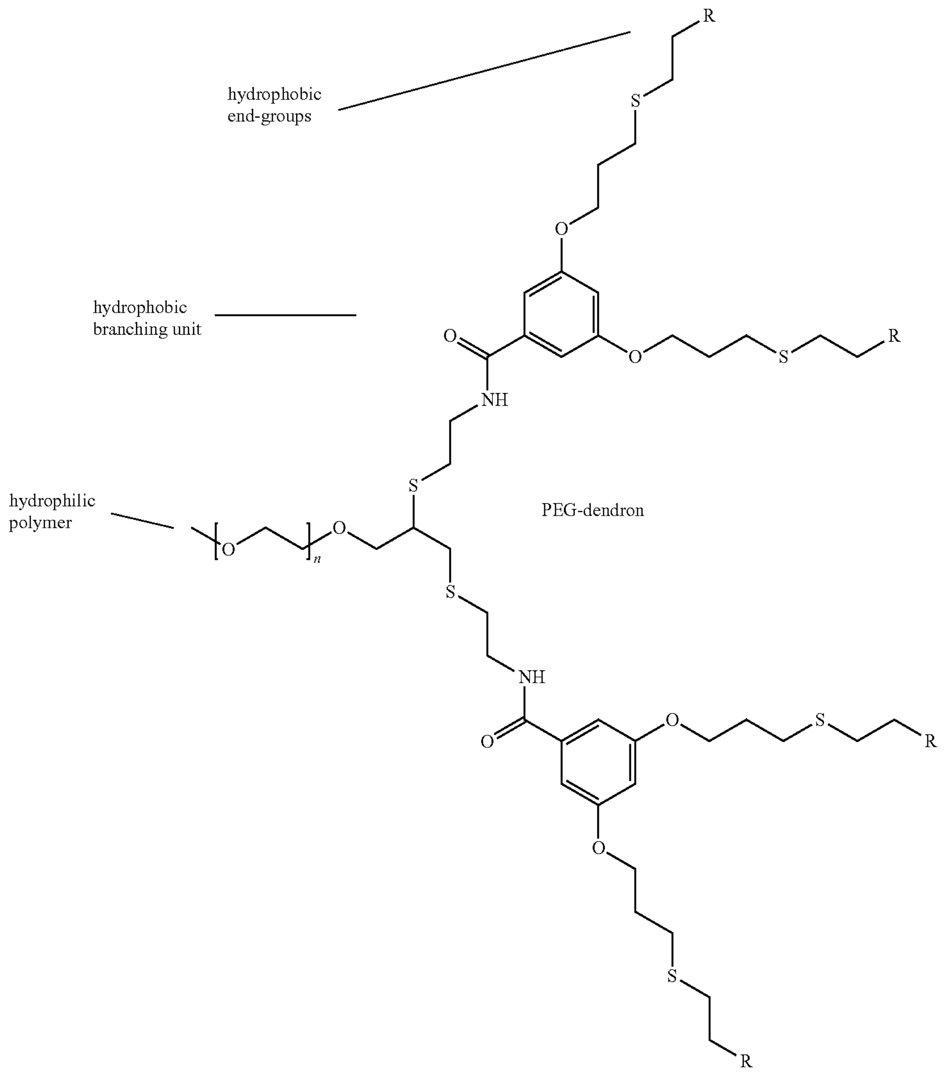

wherein R is selected from the group consisting of a naphthyl group, a naphthoate group, a pentyl group, a hexanoate group, an octanoate group, and a phenylacetamide group. Each possibility represents a separate embodiment. In some embodiments, the dendritic hybrids have structures as depicted in FIGS. 1B, 14A, 16A, and 16B. Each possibility represents a separate embodiment.

The term "alkyl" used herein alone or as part of another group denotes a saturated aliphatic hydrocarbon, including straight-chain and branched-chain alkyl groups. In one embodiment, the alkyl group has 1-12 carbons designated here as $C_1$-$C_{12}$ alkyl. In another embodiment, the alkyl group has 1-4 carbons designated here as $C_1$-$C_4$ alkyl. Examples of alkyl groups include, but are not limited to, methyl, ethyl, propyl, isopropyl, n-butyl, isobutyl, sec-butyl, t-butyl, and the like.

The term "alkylene" used herein alone or as part of another group denotes a bivalent radical which is bonded at two positions connecting together two separate additional groups (e.g., $CH_2$). Examples of alkylene groups include, but are not limited to $-(CH_2)-$, $-(CH_2)_2-$, $-(CH_2)_3-$, $-(CH_2)_4-$, etc.

The term "alkenylene" used herein alone or as part of another group denotes a bivalent radical containing at least one double bond, which is bonded at two positions connecting together two separate additional groups (e.g., $-CH{=}CH-$).

The term "alkynylene" used herein alone or as part of another group denotes a bivalent radical containing at least one triple bond, which is bonded at two positions connecting together two separate additional groups (e.g., $-C{\equiv}C-$).

The term "aryl" used herein alone or as part of another groups denotes an aromatic ring system containing from 4-14 ring carbon atoms. The aryl ring can be a monocyclic, bicyclic, tricyclic and the like. Non-limiting examples of aryl groups are phenyl, naphthyl including 1-naphthyl and 2-naphthyl, and the like.

The term "arylene" denotes a bivalent radical of aryl, which is bonded at two positions connecting together two separate additional groups (e.g., $-C_6H_4-$).

Each of the alkyl, alkylene, alkenylene, alkynylene, aryl, and arylene can be substituted by one or more of the following substituents methyl, ethyl, propyl, isopropyl, butyl, tert-butyl, halogen, haloalkyl, hydroxy, alkoxy, carbonyl, amido, alkylamido, dialkylamido, nitro, cyano, amino, alkylamino, dialkylamino, carboxyl, thio, and thioalkyl. Each possibility represents a separate embodiment.

All stereoisomers, optical and geometrical isomers of the compounds of the instant invention are contemplated, either in admixture or in pure or substantially pure form. The compounds of the present invention can have asymmetric centers at any of the atoms.

Consequently, the compounds can exist in enantiomeric or diastereomeric forms or in mixtures thereof. The present invention contemplates the use of any racemates (i.e., mixtures containing equal amounts of each enantiomer), enantiomerically enriched mixtures (i.e., mixtures enriched in one enantiomer), pure enantiomers or diastereomers, or any mixtures thereof. The chiral centers can be designated as R or S or R,S or d,D, l,L or d,l, D,L. In addition, several of the compounds of the invention contain one or more double bonds. The present invention intends to encompass all structural and geometrical isomers including cis, trans, E and Z isomers, independently at each occurrence. Any salt form with both basic and acid addition salts is also contemplated within the scope of the present invention.

Within the scope of the present invention are complexes comprising the dendritic hybrids and a single-walled carbon nanotube, wherein the hybrid polymer is non-covalently attached to the surface of the single-walled carbon nanotube through the dendron termini to form a corona capping the nanotube. The term "complex" as used herein refers to an association or a composite of a SWCNT and the dendritic hybrids, which renders the SWCNT dispersible in water. According to the principles of the present invention, the association between the dendritic hybrid and the SWCNTs is non-covalent and may include intermolecular interactions, such as, but not limited to, π-π-stacking, and van der Waals interactions. Typically, the interactions between the dendritic hybrid and the SWCNTs comprise 31-n-stacking and hydrophobic interactions between the graphene lattice of the SWCNTs and the dendritic hybrids.

According to the principles of the present invention, the association between the dendritic hybrids and the SWCNTs form a corona phase which wraps or caps the nanotube surface. It is to be understood that the degree of surface coverage by the dendritic hybrids may be full or partial, with each possibility representing a separate embodiment. Thus, in some embodiments, the surface coverage by the dendritic hybrids is at least 20% of the total SWCNTs surface area. In other embodiments, the surface coverage by the dendritic hybrids is at least 30% of the total SWCNTs surface area. In yet other embodiments, the surface coverage by the dendritic hybrids is at least 40% of the total SWCNTs surface area. In further embodiments, the surface coverage by the dendritic hybrids is at least 50% of the total SWCNTs surface area. In additional embodiments, the surface coverage by the dendritic hybrids is at least 60% of the total SWCNTs surface area. In other embodiments, the surface coverage by the dendritic hybrids is at least 70% of the total SWCNTs surface area. In yet other embodiments, the surface coverage by the dendritic hybrids is at least 80% of the total SWCNTs surface area. In various embodiments, the surface coverage by the dendritic hybrids is at least 90% of the total SWCNTs surface area.

According to some aspects and embodiments, the molar ratio between the hybrid polymer and the single-walled carbon nanotube is in the range of about $10^6$:1 to about 100:1, for example about $10^5$:1 to about $10^3$:1, including all iterations of ratios within the specified ranges. Exemplary molar ratios between the hybrid polymer and the single-walled carbon nanotube include, but are not limited to, about $10^6$:1, about $9\times10^5$:1, about $8\times10^5$:1, about $7\times10^5$:1, about $6\times10^5$:1, about $5\times10^5$:1, about $4\times10^5$:1, about $3\times10^5$:1, about $2\times10^5$:1, about $10^5$:1, about $9\times10^4$:1, about $8\times10^4$:1, about $7\times10^4$:1, about $6\times10^4$:1, about $5\times10^4$:1, about $4\times10^4$:1, about $3\times10^4$:1, about $2\times10^4$:1, about $10^4$:1, about $9\times10^3$:1, about $8\times10^3$:1, about $7\times10^3$:1, about $6\times10^3$:1, about $5\times10^3$:1, about $4\times10^3$:1, about $3\times10^3$:1, about $2\times10^3$:1, about $10^3$:1, about 900:1, about 800:1, about 700:1, about 600:1, about 500:1, about 400:1, about 300:1, about 200:1, and about 100:1. Each possibility represents a separate embodiment.

The term "single walled carbon nanotubes" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by having one of its dimensions (referred to as the length of the nanotube) elongated with respect to the other dimension (which is characterized by its diameter). It is to be understood that the term "nanotubes" as used herein refers to structures in the nanometer as well as micrometer range.

According to various embodiments, the single-walled carbon nanotubes of the present invention have diameters ranging from about 0.6 nanometers (nm) to about 100 nm and lengths ranging from about 50 nm to about 10 millimeters (mm), including each value within the specified ranges. More preferably, the single-walled carbon nanotubes have diameters ranging from about 0.7 nm to about 50 nm and lengths ranging from about 250 nm to about 1 mm, including each value within the specified ranges. Even more preferably, the single-walled carbon nanotubes have diameters ranging from about 0.8 nm to about 10 nm and lengths ranging from about 0.5 micrometer (μm) to about 100 μm, including each value within the specified ranges. Most preferably, the single-walled carbon nanotubes of the present invention have diameters ranging from about 0.9 nm to about 5 nm and lengths ranging from about 1 μm to about 50 μm, including each value within the specified ranges.

SWCNTs can be classified by the chiral vector (n,m) that characterizes the orientation of the carbon hexagons in a graphene sheet. The chiral vector of the SWCNTs can affect the adsorption of the hybrid onto its surface thereby affecting the emission signal provided therefrom. While the emission signal of the SWCNTs is in the NIR infrared spectral range, the exact wavelength depends on the chirality of the SWCNTs. By way of illustration and not limitation, chiralities of (7,6) and (8,4) produce signals at about 1,100 nm, chiralities of (9,5) and (10,3) produce signals at about 1,250 nm, and chiralities of (6,5), (7,5) and (8,3) produce signals at about 1,000 nm.

The present invention further provides a method of detecting the presence of an enzyme in a sample by exposing the complex of SWCNTs-dendritic hybrids as disclosed herein to a sample and measuring an optical property of the complex prior to and following the exposure such that the detection of a change in the optical property following exposure is indicative of the presence of the enzyme in the sample. In some embodiments, the property is an emission. In other embodiments, the emission is photoluminescence. In further embodiments, the photoluminescence is fluorescence or phosphorescence. In some embodiments, the property is emission intensity. Typically, the optical property or signal is detected in the near-infrared wavelengths in the range of about 900 to about 1,500 nm, including each value within the specified range.

In some embodiments, exposing the complex to a sample includes in vitro sensing of a laboratory sample for research, clinical diagnostics, or environmental screening. Each possibility represents a separate embodiment. Typically, the sample is a fluid, for example an aqueous solution or suspension. In other embodiments, exposing the complex to a sample includes in vivo sensing in a subject in need thereof for clinical diagnostics and monitoring. Exposing the complex to a sample can also include incubating the complex in media containing a microorganism or a cell line.

According to the principles of the present invention, determining the presence of an enzyme is performed by measuring a change in the optical property of the SWCNT upon exposure to the enzyme. As contemplated herein, the change may be reflected in the emission, the emission intensity, or the emission wavelength of the SWCNTs. Each possibility represents a separate embodiment. The change may be quantified and includes modulations (reduction or increase) of at least 5%, 10%, 15%, 20%, 25%, 30%, 35%, 40%, 45%, 50%, 55%, 60%, 65%, 70%, 75%, 80%, 85%, 90%, 95% or higher as compared to the signal prior to exposure to the enzyme. Each possibility represents a separate embodiment.

Determining the presence of an enzyme can include determining the absence of the enzyme. The present invention further provides the measurement or monitoring of an enzymatic activity, as well as identifying the presence of a pathogen excreting an enzyme in the sample. In some embodiments, determining the presence of an enzyme can include determining its concentration. In certain embodiments, relatively low concentrations or quantities of the enzyme can be determined. The ability to determine low concentrations of an enzyme may be useful, for example, in detecting trace pollutants or trace amounts of pathogens (e.g., *Salmonella*) for diagnostics and environmental applications. In some embodiments, enzymes at concentrations of less than about 100 micromolar can be detected, for example, less than about 50 micromolar, less than about 25 micromolar, less than about micromolar, or less than about 1 micromolar. Each possibility represents a separate embodiment. Continuous detection of the enzyme (i.e., monitoring) is also contemplated within the scope of the present invention. By way of illustration and not limitation, monitoring of enzymatic activity is also provided using the complexes disclosed herein.

According to some embodiments, the present invention provides a method for measuring enzymatic activity via fluorescence spectroscopy of SWCNTs dispersed in media and non-covalently bound to the dendron-polymer hybrid for use as a sensing platform comprising the steps of: functionalization of SWCNTs with a dendron-polymer hybrid to form a complex; incubating the complex for a certain period in the presence of an enzyme capable of cleaving a covalent bond between an enzymatically cleavable hydrophobic end-group and a hydrophobic branching unit of the dendron-polymer; measuring fluorescence spectroscopic properties of resulting enzymatically degraded complex and determining enzymatic activity by comparing the fluorescence spectroscopic properties of the resulting enzymatically degraded complex with an expected fluorescence spectroscopic property corresponding to a known enzymatic activity.

The complexes of the present invention can be prepared by the following method. SWCNTs are suspended in a surfactant (e.g., sodium cholate). The suspension is typically agitated (e.g., using sonication) to evenly distribute the nanotubes and prevent them from aggregating. The dendritic hybrid is then added to the suspension and the surfactant is removed by dialysis. Capping of the SWCNTs with the dendritic hybrids occurs spontaneously.

The complexes of the present invention can further be provided in the form of a kit whereby one compartment comprises the dendritic hybrids and the other compartment comprises the SWCNTs. When the hybrids are in a lyophilized form, the kit may further comprise another compartment containing an aqueous medium. According to some embodiments, associated with such compartments in the kit may be various written instructions for use.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range.

Where the stated range includes one or both of the limits, ranges excluding either or both of those included limits are also included in the invention.

As used herein, the term "about" when combined with a value refers to ±10% of the reference value.

It is noted that as used herein and in the appended claims, the singular forms "a", "an", and "the" include plural referents unless the context clearly dictates otherwise. Thus, for example, reference to "a hydrophobic end-group" includes a plurality of such hydrophobic end-groups, and so forth. It is further noted that the claims may be drafted to exclude any optional element. As such, this statement is intended to serve as antecedent basis for use of such exclusive terminology as "solely", "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a complex comprising at least one of A, B, and C" would include but not be limited to complexes that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods

Materials

Poly (ethylene glycol) methyl ether (PEG, Mn=5 kDa), 2,2-dimethoxy-2-phenylacetophenone (DMPA), allyl bromide, propargyl bromide (80% in toluene), 4-dimethylamino pyridine (DMAP), N,N'-dicyclohexylcarbodiimide (DCC), Sephadex® LH20, 2-mercaptoethanol, 3-mercaptopropionic acid, hexanoic acid, 2-napthoic acid, pentanol, 2-naphthol, cystamine dihydrochloride, phenylacetyl chloride, and Penicillin G Amidase (PGA) were purchased from Sigma-Aldrich. Sodium borohydride was purchased from Strem Chemicals. 3,5-dihydroxy benzoic acid was purchased from Apollo Scientific Ltd. 4-nitrophenol was purchased from Alfa Aesar. Triphenylmethyl chloride, potassium hydroxide and diisopropylethylamine (DIPEA) and cysteamine hydrochloride were purchased from Merck. Anhydrous potassium carbonate was purchased from J. T. Baker. Silica Gel 60 Å, 0.040-0.063 mm, sodium hydroxide and all solvents were purchased from Bio-Lab and were used as received. Deuterated solvents for NMR-analysis were purchased from Cambridge Isotope Laboratories, Inc. A UV bench lamp (UVP® Model XX-15 15 W, 365 nm UV) was used for PEG-dendron synthesis.

HiPCO single walled carbon nanotubes (SWCNT) were purchased from Nanolntegris. Porcine liver esterase (PLE), sodium cholate, and bovine serum albumin (BSA, Probumin®) were purchased from Merck. PBS buffer 10× was purchased from Hylabs and diluted to 1×PBS buffer (pH 7.4). Surfactant exchange was performed in GeBAflex dialysis devices with 3.5 kDa molecular weight cutoff (MWCO), filtering and buffer exchange of PEG-dendron capped SWCNTs was performed with Amicon centrifugal filters (MWCO: 100 kDa).

Methods $^1$H NMR

NMR-spectra were recorded on Bruker Avance I and Avance III 400 MHz ($^1$H) spectrometer. Chemical shifts are reported in ppm and referenced to the solvent. The molecular weights of the PEG-dendron hybrids were determined by comparison of the areas of the peaks corresponding to the PEG block (3.63 ppm) and the proton peaks of the dendrons.

Mass Spectrometry (MALDI-TOF MS)

Analysis was conducted on a Bruker AutoFlex MALDI-TOF MS (Germany) A DHB matrix was used.

Gel Permeation Chromatography (GPC)

All measurements were recorded on Viscotek GPCmax by Malvern using refractive index detector at 50° C. and PEG standards (purchased from Sigma-Aldrich) were used for calibration. DMF (purchased from Sigma, HPLC grade) was used as mobile phase.

Columns (2×PSS GRAM 1000 Å+PSS GRAM 30 Å) were used at a column temperature of 50° C. and samples were loaded at an injection volume of 50 μL at a flow rate of 0.5 mL/min. Samples were prepared by dissolving polymers in the mobile phase to give a final concentration of 10 mg/mL. Solutions were filtered through a 0.22 μm PTFE syringe filter.

High Performance Liquid Chromatography (HPLC)

All measurements were recorded on a Waters Alliance e2695 separations module equipped with a Waters 2998 photodiode array detector. All solvents (HPLC grade) were purchased from Bio-Lab Chemicals and were used as received.

Absorption Spectroscopy

Absorption spectra were recorded in a UV-vis-NIR spectrophotometer (Shimadzu UV-3600 Plus).

Fluorescence Measurements to Determine Critical Micellar Concentration (CMC)

CMC measurements were performed at a fluorescence spectrometer (TECAN Infinite M200Pro device) at an excitation wavelength of $\lambda_{ex}$=550 nm and an emission wavelength range of $\lambda_{em}$=580 750 nm.

NIR-Fluorescence Spectroscopy of Carbon Nanotubes

Fluorescence emission spectra were recorded in a 96-well-plate mounted on an inverted microscope (Olympus IX73). A super-continuum white-light laser (NKT-photonics, Super-K Extreme) with a bandwidth filter (NKT-photonics, Super-K varia, Δλ=nm) was coupled into the microscope as the excitation source. If not stated otherwise, spectra were recorded for SWCNT concentration of 1 mg $L^{-1}$ at an excitation wavelength of $\lambda_{ex}$=730 nm with 8.5 mW. Fluorescence emission was spectrally resolved using a spectrograph (Spectra Pro HRS-300, Teledyne Princeton Instruments) with a slit-width of 500 μm and a grating (150 g/mm). The fluorescence intensity spectrum was recorded by an InGaAs-detector (PylonIR, Teledyne Princeton Instruments) with 1 s exposure time for c(SWCNT)=5 mg $L^{-1}$ or 5 s for c(SWCNT)=1 mg $L^{-1}$. Excitation-emission maps were recorded using an excitation wavelength range of 500 nm to 840 nm in 2 nm steps.

Measuring of Fluorescence Response of SWCNT@PEG-Dendrons on Enzymatic Cleavage

Aliquots of 145 μL SWCNT@PEG-dendrons in PBS (1 mg $L^{-1}$ SWCNT concentration) were placed in a 96 well plate, and treated with PLE (final enzyme concentration of 1.5 μM), PGA (4.4 U $mL^{-1}$) or PBS for 10 h incubation time. Fluorescence emission of the samples was measured at time intervals of 30 min at an excitation wavelength of λex=730 nm. Intensity changes were determined by fitting the peaks of the spectra with a Lorentzian function.

Separation and Quantification of the Degradation Process Reaction Components of Via HPLC A total volume of 10 mL containing SWCNT@PEG-dendrons (c(SWCNT)=1 mg $L^{-1}$) and PLE (1.5 μM) or PGA (4.4 U $mL^{-1}$) and a control containing only PEG-dendrons (50 μg $mL^{-1}$) and PLE (1.5 μM) or PGA (4.4 U $mL^{-1}$) were incubated. At time intervals of 0 h, 30 min, 1 h, 2 h, 4 h, and 6 h, a volume of 1 mL was taken from the samples and subjected to 1 mL of acetonitrile to precipitate the SWCNTs while keeping the PEG-dendrons and the cleavage products in suspension. The solution was filtered with a 0.2 μm PTFE syringe filter to remove the SWCNTs. 60 μL of the samples were injected into HPLC. For the quantification of the reaction components, the peaks assigned to the intact polymer-dendrons (bearing all 4 end-groups) were integrated at absorption wavelength of: λ=225 nm (PEG-D-naphthyl); λ=236 nm (PEG-D-naphthoate); and λ=297 nm (PEG-D-pentyl and PEG-D-hexanoate). For PEG-D-naphthyl and PEG-D-naphthoate, the peaks assigned to the cleaved-off end-groups, naphthol and naphthoic acid, were integrated at absorption wavelengths of: λ=225 nm (PEG-D-naphthyl) and λ=236 nm (PEG-D-naphthoate), respectively. The concentrations of the cleaved-off end-groups were determined via a calibration curve by the area of the peak for naphthol (λ=225 nm) and naphthoic acid (λ=236 nm) at concentrations of 1, 2.5, and 5 μM. For PEG-D-pentyl and PEG-D-hexanoate, the peaks assigned to the cleaved polymer were integrated at an absorption wavelength of: λ=297 nm. The concentration of the cleaved polymers of PEG-D-pentyl and PEG-D-hexanoate was assigned, assuming full degradation of a concentration of 50 μg $mL^{-1}$.

Example 1

Synthesis

Figure 1B:
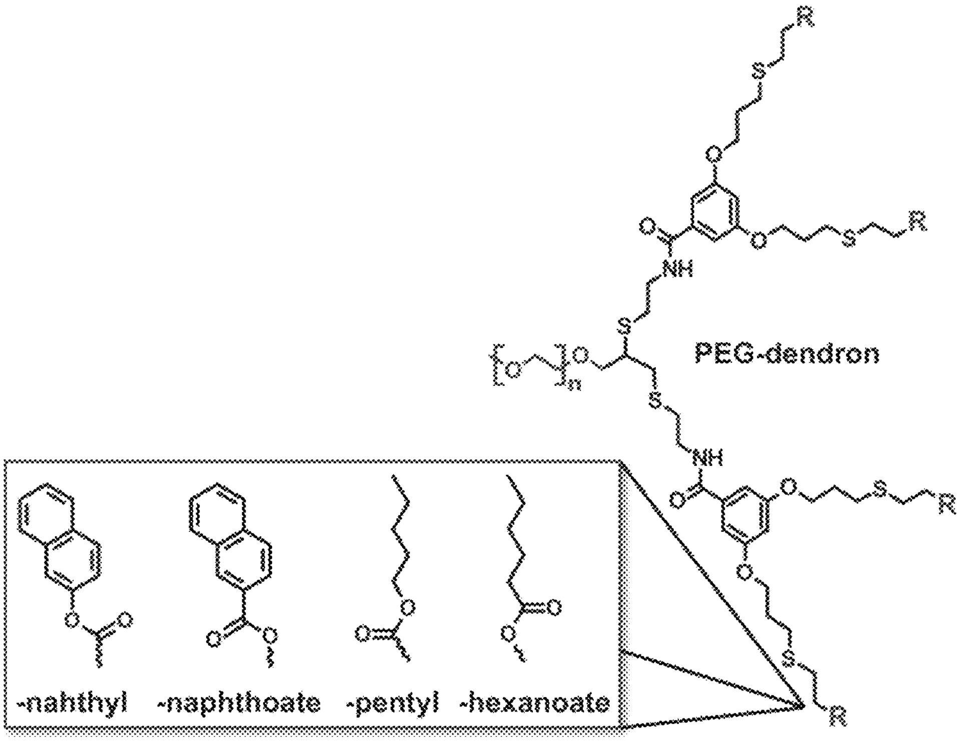

Dendron-polymer hybrids containing mono-methoxy polyethylene glycol as the hydrophilic polymer chain were prepared. The dendritic architecture exposes four hydrophobic end-groups, enabling non-covalent binding to the SWCNTs. To create a set of polymer-dendrons, two aliphatic and two aromatic (naphthalene-based) end-groups were coupled via an ester group in two different orientations to the dendritic body resulting in PEG-D-naphthyl, PEG-D-naphthoate, PEG-D-pentyl, and PEG-D-hexanoate (FIG. 1B). The orientation of the ester group in the end-groups places either an electron donor (alkoxy group of the ester) for PEG-D-naphthyl, or an electron acceptor (carbonyl group of the ester) for PEG-D-naphthoate, in the vicinity of the delocalized it-electron system of the aromatic end-group affecting its electron density. Due to their aromatic nature, these end-groups bind to the SWCNTs via π-π-stacking interactions, which are influenced by the electron density of the delocalized π-systems. In contrast, the aliphatic end-groups interact with the SWCNTs via hydrophobic interactions. Hence, the orientation of the ester group does not affect the binding interaction. To avoid an effect due to changes in molecular weight, each couple of amphiphiles, was synthesized to have exactly the same molecular weight. This was achieved by reacting 3-mercaptopropionic acid with the 2-naphthol and pentanol for synthesizing the naphthyl and pentyl end-groups, respectively, while using 2-mercaptoethanol for preparing the 2-naphthoate and hexanoate end-groups.

In particular, PEG-dendrons were synthesized from three building blocks: methoxy diamino PEG, PNP-$AB_2$-branching unit, and the five different thiols functionalization which are enzymatically cleavable end-groups. The coupling of the building blocks was performed in a two-step synthesis. The polymer was coupled to the dendron body via an amide coupling followed by coupling of the end-groups to the dendron body via a UV-mediated thiol-ere coupling reaction. The purity of the synthesized hybrids was determined using NMR-spectroscopy. The molecular mass and the poly dispersity of the resulting PEG-dendron hybrids were analyzed using MALDI-TOF-mass spectrometry and GPC. The critical micellar concentration was measured using a fluorescence probe, Methoxy diamino PEG [$mPEG_{5kDa}$-$(NH_2)_2$] was synthesized in two steps as described in Scheme 1. Synthesis initiated with an $S_N2$ reaction of $mPEG_{5kDa}$-OH with propargyl bromide to give $mPEG_{5kDa}$-propargyl, which was then followed by the thiol-yne reaction with cysteamine hydrochloride to obtain the desired methoxy diamino PEG [$mPEG_{5kDa}$-$(NH_2)_2$].

Scheme 1.

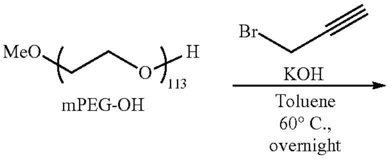

mPEG-OH

-continued

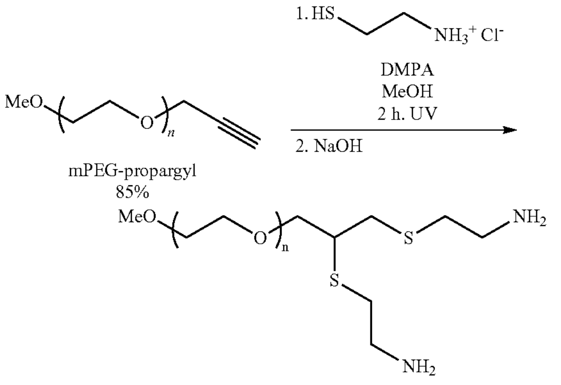

mPEG-propargyl
85% mPEG-$(NH_2)_2$
89%

The active 4-nitrophenol ester of the $AB_2$ branching unit (PNP-$AB_2$) was prepared from 3,5-dihydroxy benzoic acid (3,5-DHB) using two reactions as described in Scheme 2. First, 3,5-DHB was fully reacted with allyl bromide and then the formed allyl ester was hydrolyzed in situ to give HOOC-$AB_2$ in excellent yield. In the second step, the free acid was activated to a 4-nitrophenol ester under Steglich esterification conditions with 4-nitrophenol (PNP).

Scheme 2.

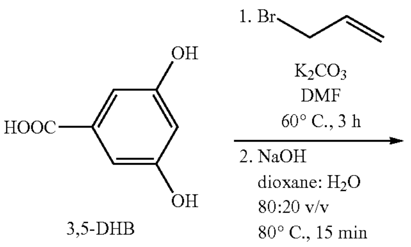

3,5-DHB

-continued

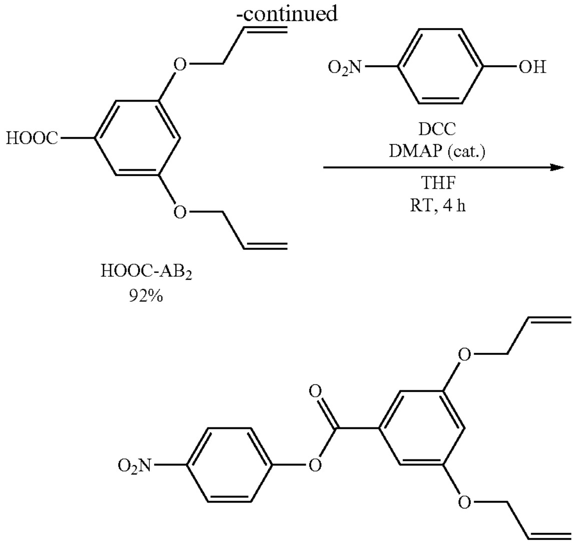

HOOC-$AB_2$
92%

PNP-$AB_2$
98%

The branches containing the enzymatically cleavable end-groups were synthesized in two different ways, as shown in Scheme 3. For the esterase cleavable end-group, the thiol functional group of 3-mercaptopropionic acid and 2-mercaptoethanol were masked with trityl group, followed by Steglich esterification reaction with specific acid or alcohol/phenol containing functional groups. In the last step, the trityl protecting group was removed by treating it with strong acid (trifluoroacetic acid, TFA) in the presence of triethyl silane ($Et_3SiH$) as a scavenging agent for triphenylmethyl carbocation.

For the amidase cleavable end-groups, phenylacetyl chloride was added dropwise to a solution of cystamine dihydrochloride in water. The disulfide thus obtained was reduced by adding sodium borohydride in ethanol:water (5:3 v/v), then acidified to pH 2 with dilute hydrochloric acid.

Scheme 3.

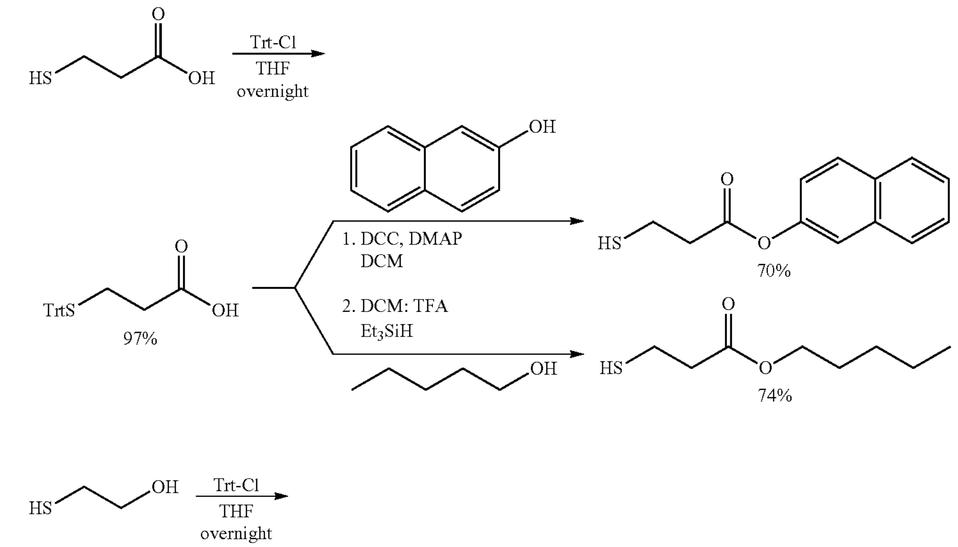

-continued

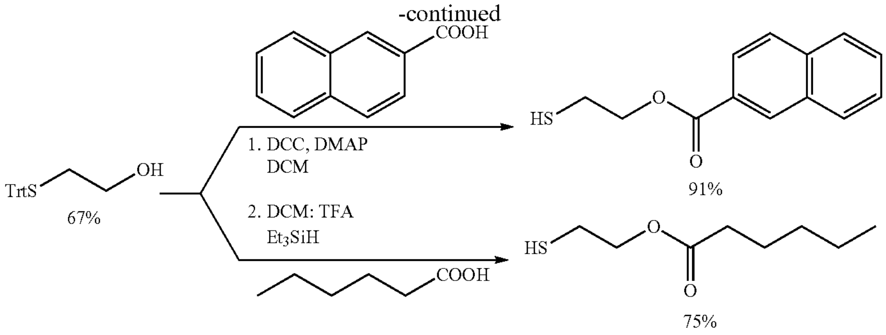

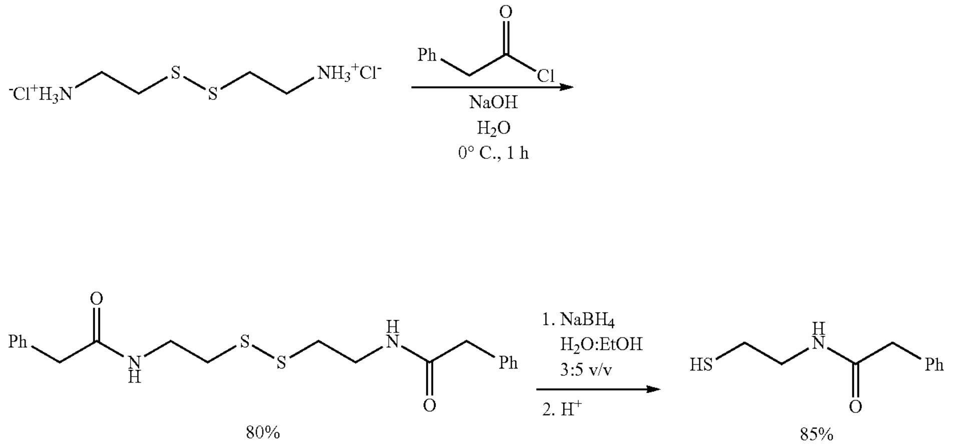

For the coupling of the polymer with the dendritic branching unit, $mPEG_{5kDa}$-$(NH_2)_2$ was dissolved in DCM:DMF 1:1 v/v (1 mL per 100 mg PEG). DIPEA (18 eq.) and 4-nitrophenyl ester of the branching unit ($PNP-AB_2$, 6 eq.) were added and the reaction was stirred overnight at room temperature. The reaction mixture was loaded on a LH20 (Sephadex®) size exclusion column and eluted with methanol. Fractions that contained the product (identified by UV light and/or $I_2$ staining) were unified and the solvent was evaporated to dryness. In order to facilitate the solidification of the product, the oily residue was re-dissolved in DCM (1 mL per 100 mg PEG) and hexane (5 mL per 100 mg PEG) was added. Organic solvents were evaporated to dryness and the obtained solid was dried under high vacuum, to obtain m-PEG-[deed-$(ene)_2]_2$.

Scheme 4.

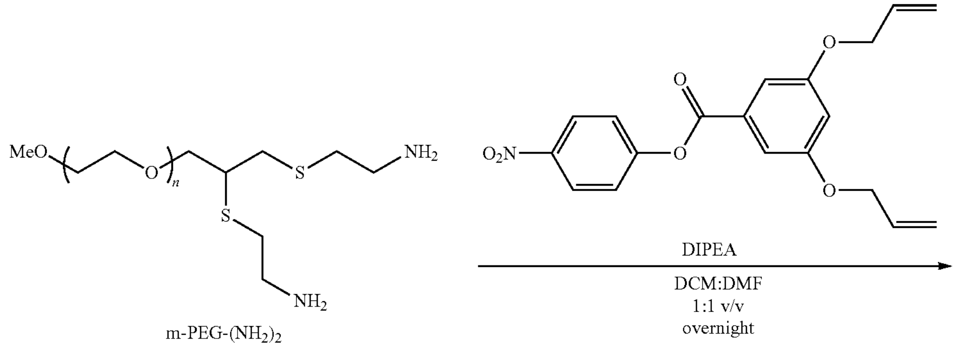

m-PEG-$(NH_2)_2$

-continued

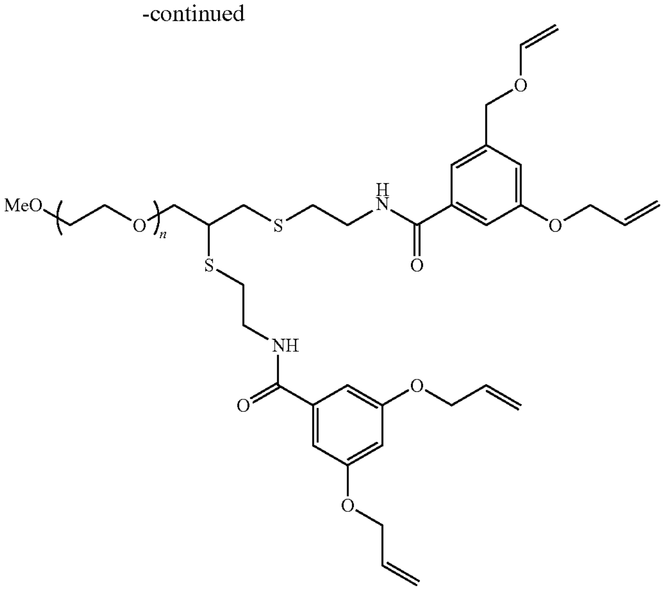

m-PEG-[dend-(ene)2]2
87%

The PEG reactant was dissolved in DMF (5 mL/g PEG) using gentle heating. Thiol-functionalized end-group (10 eq. per double bond) and DMPA (0.1 eq. per double bond) were added. The clear solution was purged with $N_2$ for 30 minutes and then placed under UV light for 2 h. The reaction was loaded as-is on a MeOH-based LH20 column (Sephadex®). Fractions that contained the product (identified with UV or I2 coloring) were unified and the solvent was evaporated to dryness and the product was dried under high vacuum.

Scheme 5.

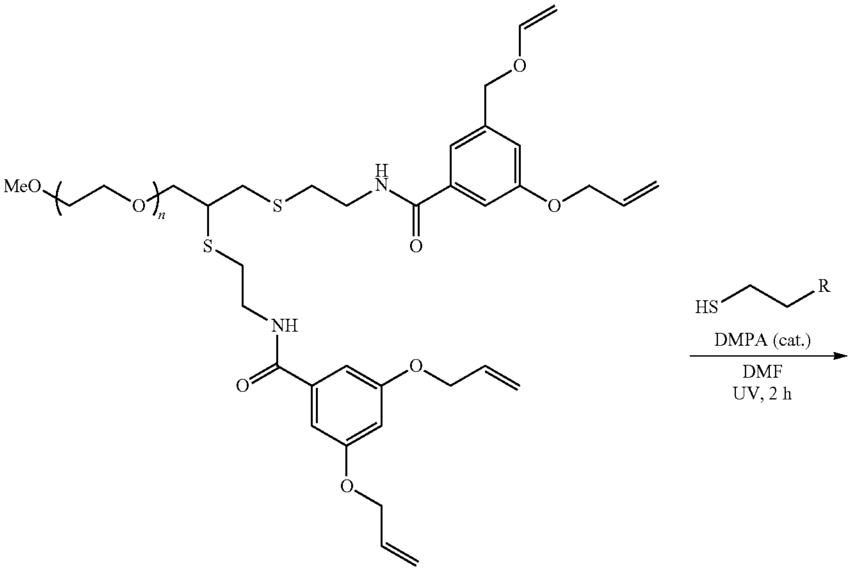

m-PEG-[dend-(ene)2]2

-continued

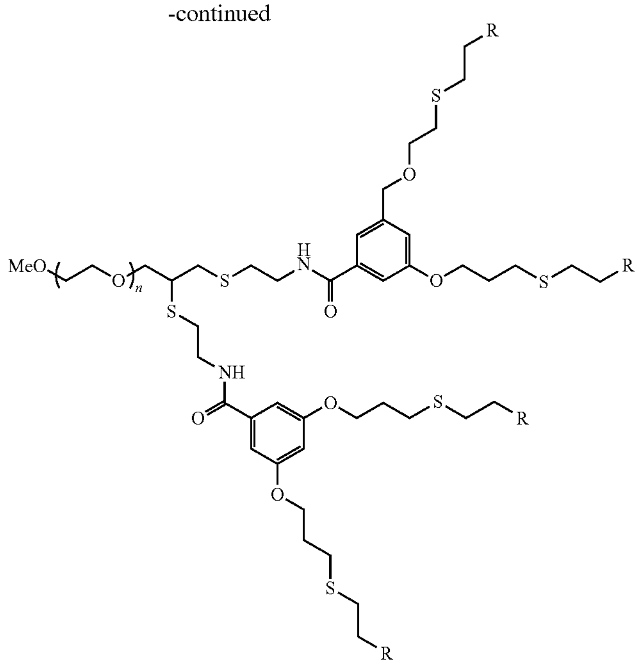

R =

| | | |
|---|---|---|
| 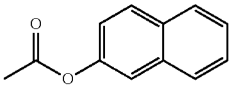 | PEG-D-naphthyl | 87% |
| 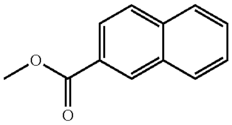 | PEG-D-naphthoate | 87% |
| 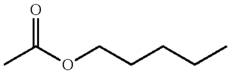 | PEG-D-pentyl | 93% |
| 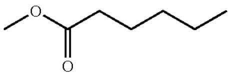 | PEG-D-hexanoate | 93% |
| 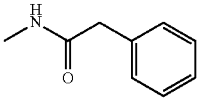 | PEG-D-phenylacetamide | 95% |

mPEG-[dend-(naphthyl)$_2$]$_2$ termed PEG-D-naphthyl was prepared as follows. 200 mg of m-PEG-[dend-(ene)$_2$]$_2$ was reacted with naphthalen-2-yl 3-mercaptopropanoate (325 mg, 1.4 mmol, 40 eq.) and DMPA (3.6 mg, 0.014 mmol, 0.4 eq.). The product was obtained as a white solid in 87% yield (200 mg). $^1$H-NMR ($CDCl_3$): δ 7.87-7.82 (m, 8H, Ar—H), 7.81-7.76 (m, 4H, Ar—H), 7.55 (d, J=2.4 Hz, 4H, Ar—H), 7.51-7.45 (m, 8H, Ar—H), 7.23 (dd, J=8.9, 2.4 Hz 4H, Ar—H), 6.95 (dd, J=4.2, 2.2 Hz 4H, Ar—H), 6.57 (s, 2H, Ar—H), 4.01 (t, J=5.9 Hz 8H, Ar—O—$CH_2$), 3.84-3.47 (m, PEG backbone), 3.39 (s, 3H, $CH_3$—O-PEG), 3.09-2.57 (m, 31H, —CH—S+—$CH_2$—S+—CO—$CH_2$—$CH_2$—S), 2.10-2.02 (m, 8H, Ar—O—$CH_2$—$CH_2$). GPC (DMF): Mn=5.2 kDa, ĐM=1.08. Expected Mn=6.5 kDa. MALDI-TOF MS: molecular ion centered at 6.7 kDa.

mPEG-[dend-(naphthoate)$_2$]$_2$ termed PEG-D-naphthoate was prepared as follows. 200 mg of m-PEG-[dend-(ene)$_2$]$_2$ was reacted with 2-mercaptoethyl 2-naphthoate (325 mg, 1.4 mmol, 40 eq.) and DMPA (3.6 mg, 0.014 mmol, 0.4 eq.). The product was obtained as a white solid in 87% yield (200 mg). $^1$H-NMR ($CDCl_3$): δ 8.60-8.54 (m, 4H, Ar—H), 8.02 (dd, J=8.6, 1.7 Hz 4H, Ar—H), 7.95-7.90 (m, 4H, Ar—H), 7.85 (d, J=8.4 Hz, 8H, Ar—H), 7.60-7.49 (m, 8H, Ar—H), 6.92 (dd, J=3.3, 2.2 Hz 4H, Ar—H), 6.51 (t, J=2.2 Hz 2H, Ar—H), 4.51 (t, J=7.0 Hz 8H, Ar—COO—$CH_2$), 3.97 (t, J=6.1 Hz 8H, Ar—O—$CH_2$), 3.81-3.45 (m, PEG backbone), 3.37 (s, 3H, $CH_3$—O-PEG), 2.93-2.70 (m, 23H, —CH—S+—$CH_2$—S), 2.06-1.98 (m, 8H—Ar—O—$CH_2$—$CH_2$). GPC (DMF): Mn=5.6 kDa, ĐM=1.08. Expected Mn=6.5 kDa. MALDI-TOF MS: molecular ion centered at 6.7 kDa.

mPEG-[dend-(pentyl)$_2$]$_2$ termed PEG-D-pentyl was prepared as follows. 200 mg of m-PEG-[dend-(ene)$_2$]$_2$ was reacted with pentyl 3-mercaptopropanoate (250 mg, 1.4 mmol, eq.) and DMPA (3.6 mg, 0.014 mmol, 0.4 eq.), The product was obtained as a white solid in 93% yield (210 mg). $^1$H-NMR ($CDCl_3$): δ 6.92 (dd, J=3.4, 2.2 Hz 4H, Ar—H), 6.53 (t, J=2.2 Hz, 2H, Ar—H), 4.08 (t, J=6.8 Hz 8H, —COO—$CH_2$), 3.99 (t, J=6.8 Hz 8H, Ar—O—$CH_2$), 3.82-3.53 (m, PEG backbone), 3.37 (s, 3H, $CH_3$—O-PEG), 3.18-2.51 (m, 31H, —CH—S+—$CH_2$—S+—CO—$CH_2$—$CH_2$—S), 2.02 (qui, J=6.4 Hz 8H, Ar—O—$CH_2$—$CH_2$), 1.66-1.58 (m, 8H, —COO—$CH_2$—$CH_2$), 1.32 (dq, J=7.2, 4.0, 3.3 Hz 16H, —COO—$(CH_2)_2$—$CH_2$+—COO—$(CH_2)_3$—$CH_2$), 0.89 (t, J=4.6 Hz 12H, —COO—$(CH_2)_4$—$CH_2$). GPC (DMF): Mn=5.8 kDa, ĐM=1.09. Expected Mn=6.3 kDa. MALDI-TOF MS: molecular ion centered at 6.4 kDa.

mPEG-[dend-(hexanoate)$_2$]$_2$ termed PEG-D-hexanoate was synthesized as follows, 200 mg of m-PEG-[dend-(ene)$_2$]$_2$ was reacted with 2-mercaptoethyl hexanoate (250 mg, 1.4 mmol, 40 eq.) and DMPA (3.6 mg, 0.014 mmol, 0.4 eq.). The product was obtained as a white solid in 93% yield (210 mg). $^1$H-NMR ($CDCl_3$): δ 6.92 (dd, J=3.4, 2.2 Hz 4H, Ar—H), 6.53 (t, J=2.2 Hz, 2H, Ar—H), 4.21 (t, J=7.0 Hz 8H, —COO—$CH_2$), 4.00 (t, J=6.8 Hz 8H, Ar—O—$CH_2$), 3.82-3.44 (m, PEG backbone), 3.37 (s, 3H, $CH_3$—O-PEG), 3.14-2.62 (m, 17H, —CH—S+—$CH_2$—S), 2.30 (t, J=7.5 Hz 8H, —O—CO—$CH_2$), 2.01 (qui, J=6.4 Hz 8H, Ar—O—$CH_2$—$CH_2$), 1.65-1.57 (m, 8H, —O—CO—$CH_2$—$CH_2$), 1.36-1.23 (m, 16H, —O—CO—$(CH_2)_2$—$CH_2$+—O—CO—$(CH_2)_3$—$CH_2$), 0.87 (t, J=4.6 Hz 12H, —O—CO—$(CH_2)_4$—$CH_2$). GPC (DMF): Mn=5.8 kDa, ĐM=1.09. Expected Mn=6.3 kDa. MALDI-TOF MS: molecular ion centered at 6.5 kDa.

mPEG-[dend-(PhAcAm)$_2$]$_2$ termed PEG-D-phenylacetamide was prepared as follows. 200 mg of m-PEG-[dend-(ene)$_2$]$_2$ was reacted with N-(2-mercaptoethyl)-2-phenylacetamide (278 mg, 1.4 mmol, 40 eq.) and DMPA (3.6 mg, 0.014 mmol, 0.4 eq.). The product was obtained as a white solid in 95% yield (216 mg). $^1$H-NMR ($CDCl_3$): δ 7.67-7.92 (m, 2H, —NH—CO—), 7.27-7.41+7.10-7.25 (m, 20H, Ph), 6.86-6.99 (m, 4H, Ar H), 6.42-6.53 (m, 2H, Ar H), 5.99-6.23 (m, 4H, —NH—CO—), 3.83-3.94 (m, 8H, Ar—O—$CH_2$—), 3.43-3.81 (m, PEG backbone), 3.28-3.40 (m, 11H, —O—$CH_3$+—$CH_2$—NH—CO—), 3.02-3.28 (m, 1H, —CH—S—), 2.43-2.94 (m, 22H, —$CH_2$—S—), 1.90 (qui, J=6.6 Hz, 8H, —O—$CH_2$—$CH_2$—$CH_2$—S—). GPC (DMF): Mn=6.1 kDa, ĐM=1.05. Expected Mn=6.4 kDa.

Example 2

Characterization of Hybrids

Critical Micelle Concentration (CMC) value of each hybrid was measured using Nile red as a solvatochromic fluorescent probe, whose fluorescence emission intensity depends on the polarity of its environment. Diluent solution was prepared by adding 45 μL of a Nile red stock solution (0.88 mg/mL in ethanol) into 100 mL PBS (pH 7.4) followed by mixing to obtain a final concentration of 1.25 μM. The determination of CMC for all PEG-dendrons was performed as follows: A 500 μM solution of the PEG-dendron was prepared in a diluent. The solution was vortexed and sonicated for 15 min until a clear solution was obtained. The solution was repeatedly diluted with a diluent by a factor of 1.5 to obtain a series of 24 samples. 150 μL of each solution were loaded onto a 96 wells plate. Fluorescence emission intensity was performed for each well. The maximum emission intensity at about 63 nm was plotted vs. hybrid's concentration in order to determine the CMC (Table 1). All measurements were repeated 3 times. The CMC values were shown to slightly increase when the hydrophobicity of the end-group decreased. Thus, it is contemplated that PEG-D-naphthyl and PEG-D-naphthoate hybrids exhibit a slightly higher tendency to form micelles at lower concentrations than PEG-D-pentyl and PEG-D-hexanoate hybrids.

TABLE 1

Critical micelle concentrations of the PEG-dendrons

| PEG-dendron~ | CMC |
|---|---|
| naphthyl | 13 ± 6 μg/mL |
| naphthoate | 13 ± 6 μg/mL |
| pentyl | 25 ± 6 μg/mL |
| hexanoate | 19 ± 6 μg/mL |
| phenylacetamide | 45 ± 6 μg/mL |

Example 3

Capping of SWCNTs by PEG-Dendrons Hybrids

Figure 1C:
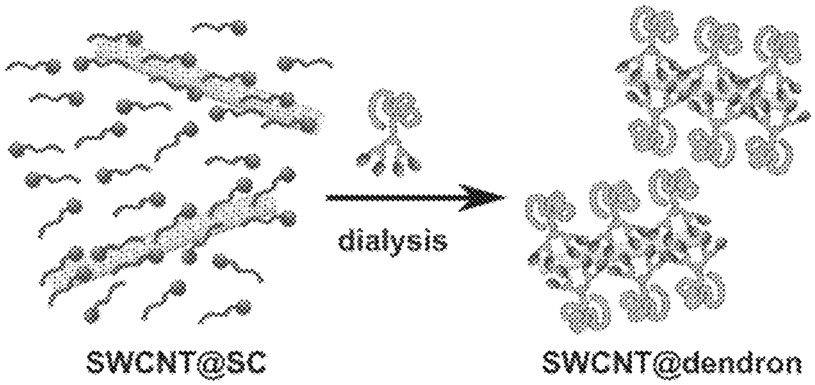
Figure 1D:
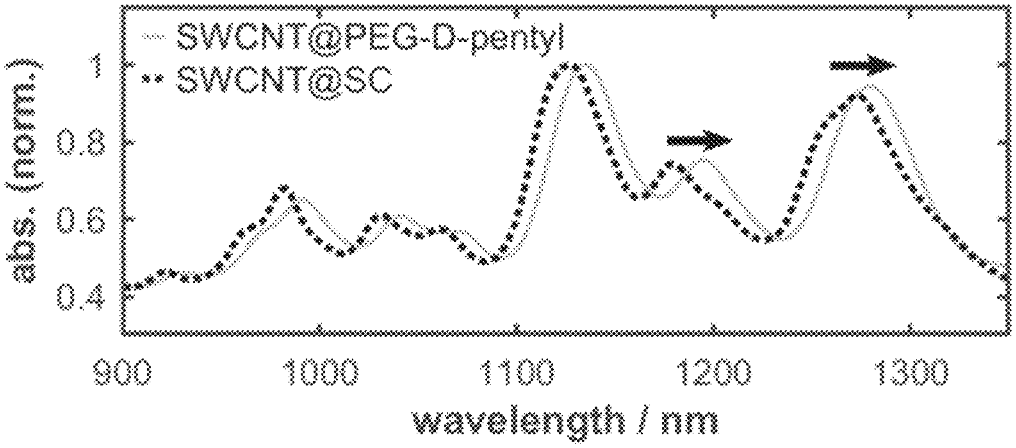
Figure 2A:
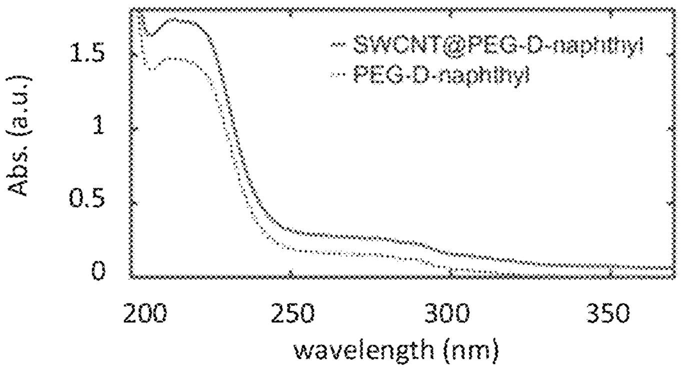
FIGS. 2A-2D show UV-absorption spectra of SWCNT@PEG-dendrons (solid lines) and free PEG-dendrons (dashed lines).
Figure 2B:
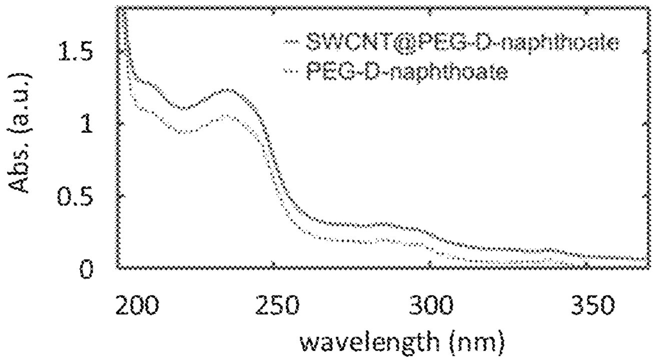
Figure 2C:
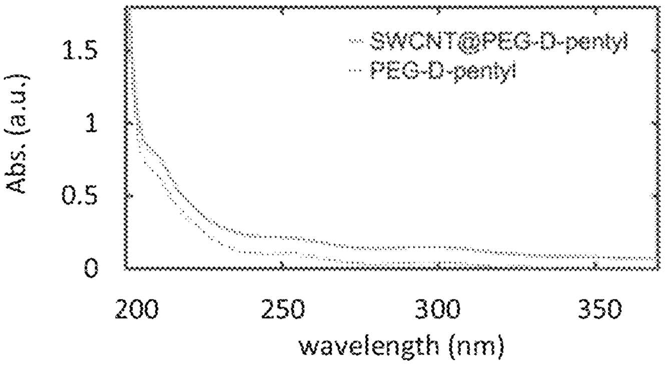
Figure 2D:
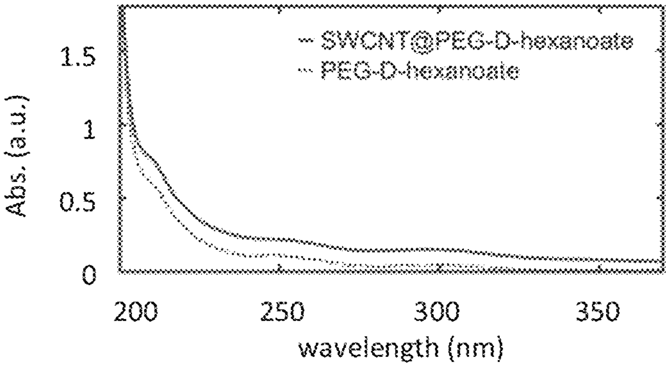

Functionalization of the SWCNTs was achieved via surfactant exchange, where sodium etiolate suspended SWCNTs (SWCNT@SC), together with the respective polymer-dendron, were dialyzed against water, to slowly remove sodium cholate allowing the PEG-dendrons to non-covalently bind the SWCNTs and stabilize them in suspension (FIG. 1C). In particular, HiPCO-SWCNT powder was suspended in water at a concentration of 2 mg $mL^{-1}$. In order to suspend the SWCNTs with sodium cholate (SC), a mixture containing 10 mg of HiPCO SWCNTs in 20 mL of 2% (w/v) sodium cholate was bath sonicated for 10 min and subsequently tip sonicated for 2×30 min on ice (12 W). The resulting suspension was ultracentrifuged for 4 h at 40,000 g (Optima XPN-80 ultracentrifuge, Beckman Coulter) to remove nanotube bundles and impurities. The concentration of SWCNT@SC suspension was determined spectroscopically (c(SWCNT@SC)=220 mg $L^{-1}$) with an extinction coefficient of $\varepsilon_{632\ nm}$=0.036 $L\cdot mg^{-1}\cdot cm^{-1}$.

A suspension of SWCNT@SC (40 mg $L^{-1}$) in 2% (w/v) sodium cholate and the respective PEG-dendron (2 mg $L^{-1}$) in a total volume of 7 mL were transferred into a dialysis device (GeBAflex Mega, 3.5 kDa MWCO). The carbon nanotube suspension was dialyzed against water for 5 days, to remove the sodium cholate. After dialysis, HiPCO@PEG-dendron was centrifuged for 30 min at 20,000 g to remove aggregates. The supernatant suspension was washed 3 times with PBS buffer (pH 7.4) in an Amicon centrifugal filter (100 kDa MWCO, 25 min, 4,400 g), and the suspension was stored in PBS buffer. The concentrations of SWCNT@PEG-dendrons were determined spectroscopically via their extinction coefficient ($\varepsilon_{632\ nm}$=0.036 $L\cdot mg^{-1}\cdot cm^{-1}$).

The spectra of the SWCNT@PEG-dendrons (1 mg $L^{-1}$) and the free PEG-dendrons at c=50 μg $mL^{-1}$ show comparable UV-absorption. Accordingly, it was determined that no significant loss of PEG-dendrons after surfactant exchange occurred (FIGS. 2A-2D). Higher absorption in the spectra of SWCNT@PEG-dendrons, compared to the respective PEG-dendron without the SWCNTs is contemplated to stem from additional UV-VIS absorption of the SWCNTs. The integrated areas of the initial (t=0 h) intact PEG-dendrons after separation as determined using HPLC, show comparable results (Table 2).

TABLE 2

| Comparing the area of the intact polymer with and without SWCNTs at t = 0 h | naphthyl [$\cdot 10^6$] | naphthoate [$\cdot 10^6$] | pentyl [$\cdot 10^4$] | hexanoate [$\cdot 10^4$] |
|---|---|---|---|---|
| Integrated area (SWCNT @ PEG-dendron) | (2.45 ± 0.038) | (1.91 ± 0.014) | (4.75 ± 0.11) | (4.75 ± 0.11) |
| Integrated area (free PEG-dendrons) | (2.26 ± 0.040) | (2.00 ± 0.033) | (4.52 ± 0.14) | (4.08 ± 0.03) |

Figure 3A:
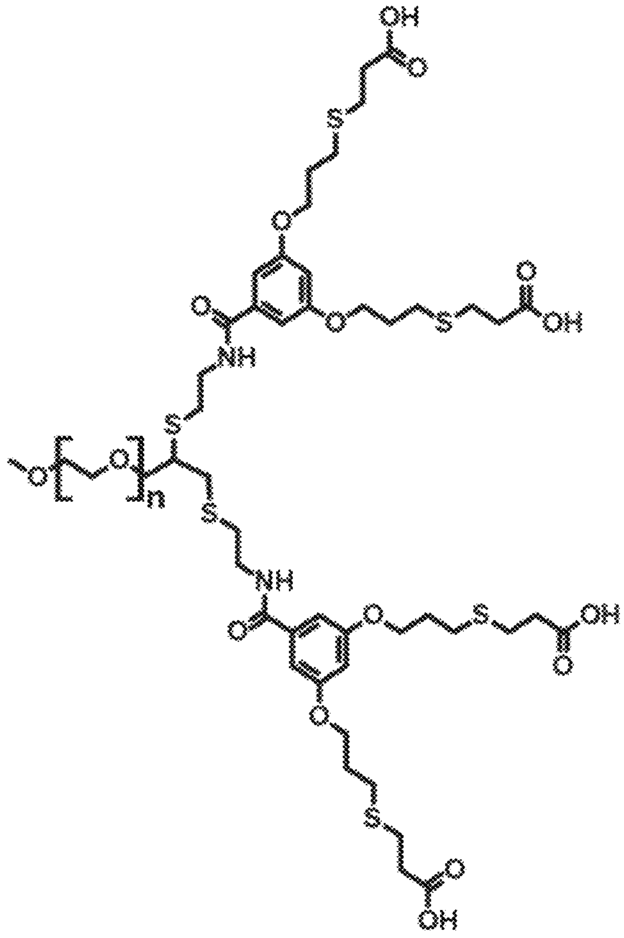
FIGS. 3A-3B show surfactant exchange of carbon nanotubes with PEG-dendron hybrids lacking the hydrophobic end-group.
Figure 3B:
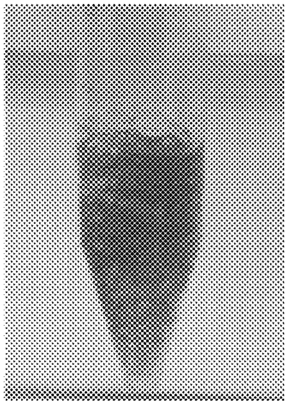
Figure 4A:
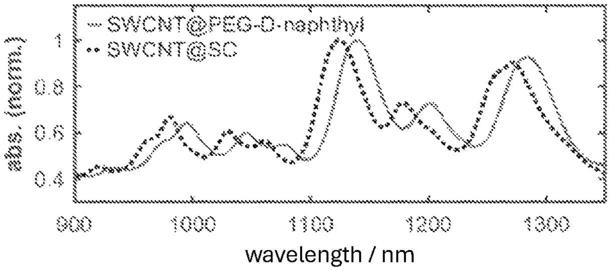
Figure 4B:
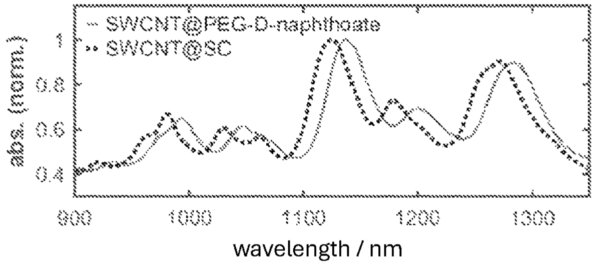
Figure 4C:
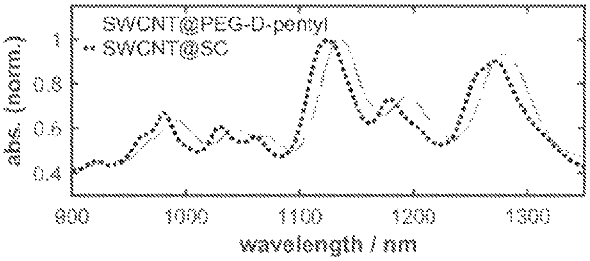
Figure 4D:
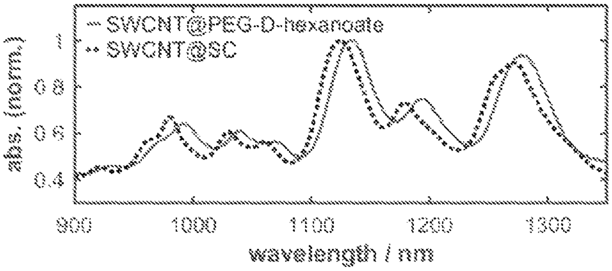
Figure 5A:
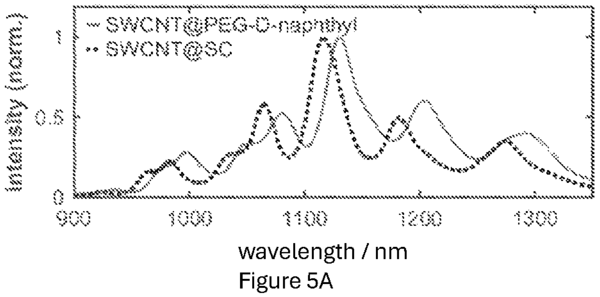
Figure 5B:
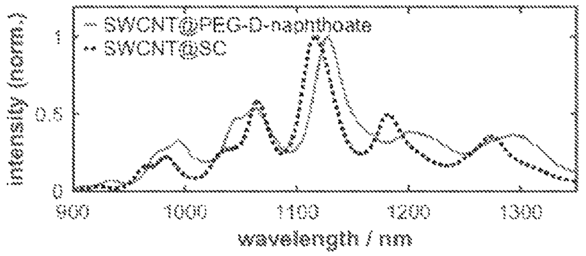
Figure 5C:
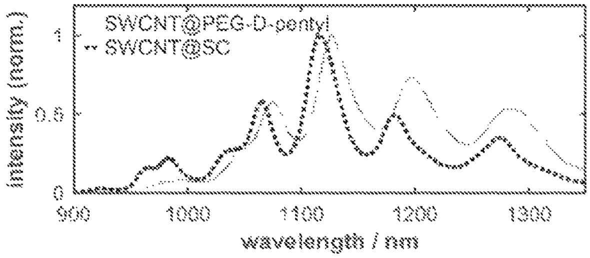
Figure 5D:
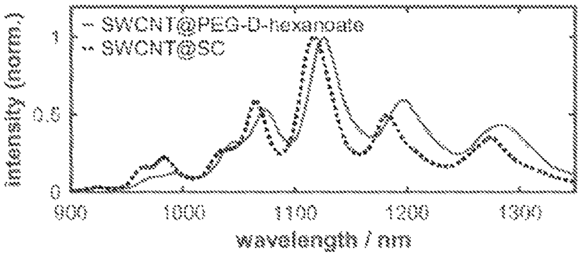

To ensure the critical role of the hydrophobic end-groups in suspending the SWCNTs, the surfactant exchange was also performed with a PEG-dendron bearing hydrophilic end-groups as a control (FIG. 3A). This experiment resulted in SWCNTs aggregation (FIG. 3C) upon removal of sodium cholate during dialysis in the presence of PEG-D-COOH showing that PEG-D-COOH cannot suspend SWCNTs in aqueous solution. It is therefore concluded that the hydrophobic end-groups are essential for stabilizing the suspended SWCNTs.

The NIR-absorption spectra of the resulting PEG-dendron capped SWCNTs (SWCNT@PEG-dendron) showed a red-shift of the $E_{11}$-absorption peaks (FIGS. 1D and 4A-4D) as well as of the fluorescence emission of the SWCNT chiralities (FIGS. 5A-5D compared to SWCNT@SC, indicating a successful exchange of the capping consistent with a change in the dielectric environment of the SWCNTs.

Figure 6A:
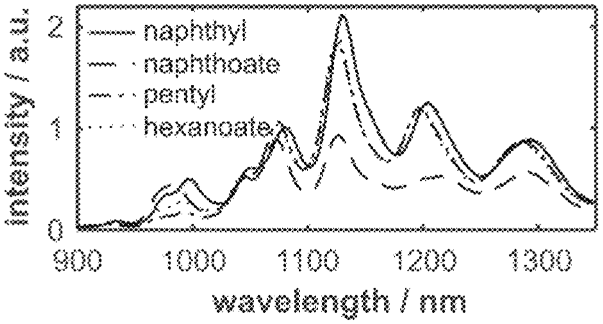
FIGS. 6A-6D show a comparison between absorption and fluorescence spectra of the different SWCNT@PEG-dendrons.
Figure 6B:
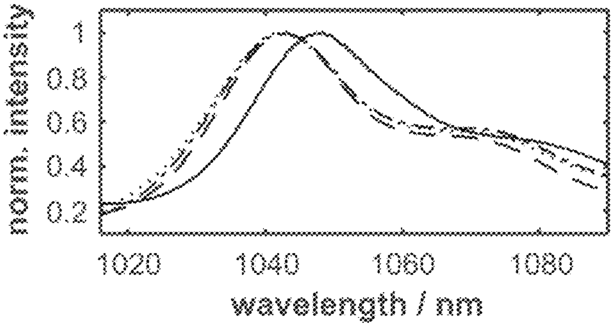
Figure 6C:
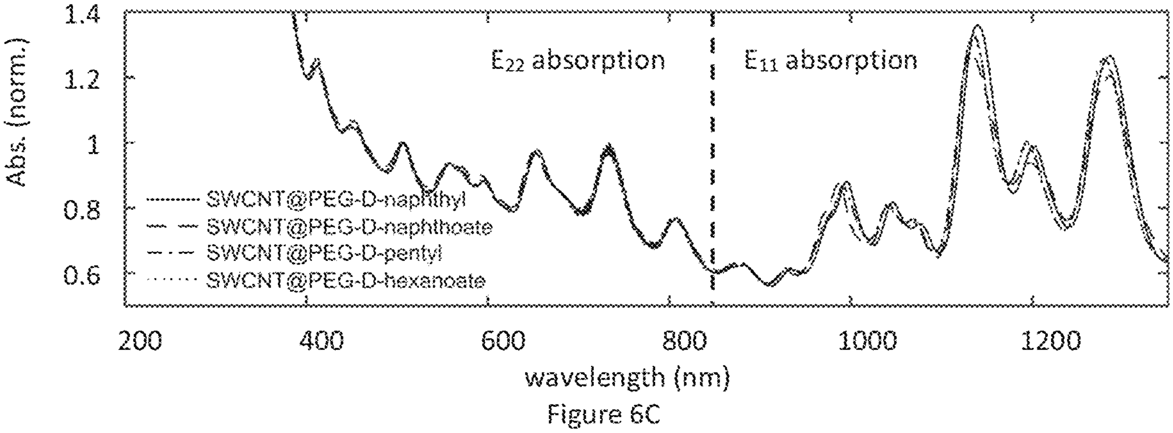
Figure 6D:
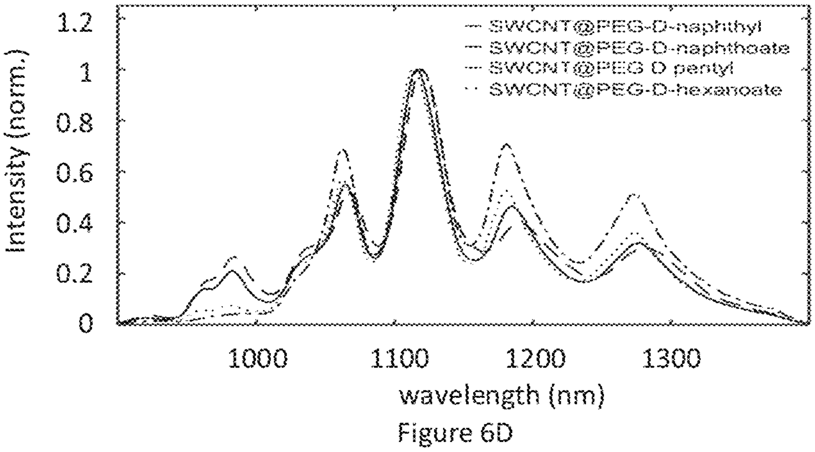
Figure 7I:
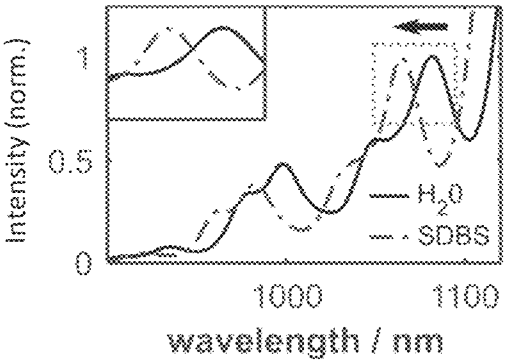
Figure 7J:
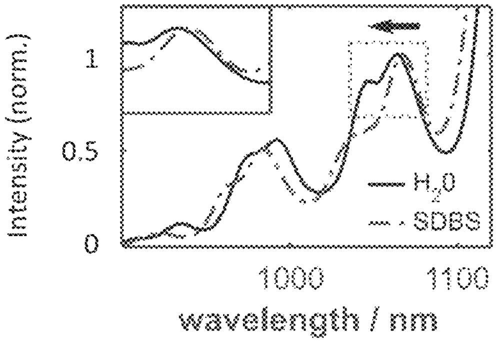
Figure 7K:
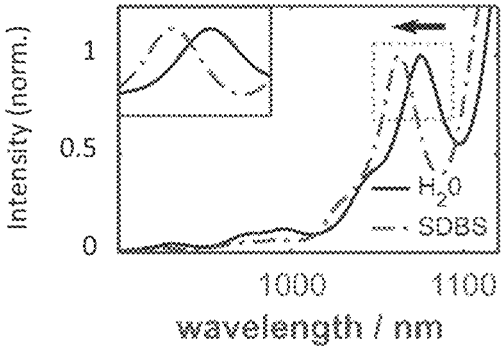
Figure 7L:
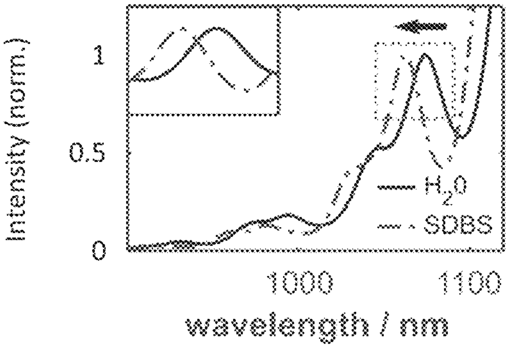

The red-shift of the $E_{11}$-absorption peaks and the fluorescence emission of the SWCNT chiralities were induced by the non-covalent binding of the PEG-dendrons to the SWCNTs via the end-groups of the dendrons. The interactions of the end-groups with the graphene lattice are different for each type of end-group. While π-π-stacking of the SWCNT with the aromatic end-groups is possible, hydrophobic interactions are more likely to occur in aliphatic end-groups. These differences in interactions between the end-groups and the SWCNTs are reflected in the different fluorescence emission spectra of the SWCNT@PEG-dendrons. FIGS. 6A-6B show a relatively lower fluorescence intensity of the SWCNT@PEG-D-naphthoate and a red-shifted emission wavelengths of the SWCNT@PEG-D-naphthyl compared to the other SWCNT@PEG-dendrons (shown for the (10,2) chirality). While the four SWCNT@PEG-dendrons show comparable absorption spectra of the $E_{22}$-transitions, substantial differences in their fluorescence emission spectra of the $E_{11}$-transitions were observed, although all four samples were prepared from the same initial SWCNT@SC suspension (FIG. 6C).

FIGS. 7A-7H show the NIR-fluorescence emission recorded for excitation wavelengths of $\lambda_{ex}$=500-840 nm for the four different SWCNT@PEG-dendrons and the differences in the normalized fluorescence emission between the two PEG-dendrons with aromatic end-groups and those with aliphatic end-groups. The orientation of the ester-groups in the two PEG-dendrons with aromatic end-groups, and the resulting difference of their electron density on π-π-stacking interactions had a substantial effect on the SWCNT fluorescence modulation. The fluorescence intensity of SWCNT@PEG-D-naphthoate, which has electron withdrawing groups, is relatively lower, and the emission wavelength peaks of the different chiralities of the SWCNT@PEG-D-naphthyl, which has electron donating groups, are red-shifted, compared to the other SWCNT@PEG-dendrons (FIGS. 6A-6C and 7A-7H). However, for the two PEG-dendrons with aliphatic end-groups, comparable fluorescence emission was observed, both in intensity and wavelength, since the orientation of the ester-groups has no effect on the hydrophobic interactions. Comparing the fluorescence spectra of the aromatic SWCNT@PEG-dendrons with their aliphatic counterparts, substantially higher fluorescence emission of the small-diameter (8,3) and (6,5) chiralities (FIGS. 7A-7H) for the aromatic amphiphiles was observed. These variations cannot be attributed to simple differences in the concentration of the chiralities within the samples, as evident from the similar absorption spectra (FIGS. 6A-6D). Rather, these variations are attributed to the distinct chemical properties of the end-groups. The excitation-emission maps reveal the differences in the interaction of the dendritic end-groups with the SWCNT surface.

The addition of surfactants, e.g., sodium dodecylbenzenesulfonate (SDBS), to functionalized SWCNTs can provide information both about the available, exposed surface area of the SWCNTs, and the binding affinity of the dendrons to the SWCNTs by inducing a solvatochromic shift (Δλ) upon the replacement of water molecules and possibly some of the dendritic amphiphiles in case their binding affinity is lower than the binding affinity of the surfactant (Chio et al., Nano Lett. 2019, 19, 7563-7572; Harvey et al., Nat. Biomed. Eng. 2017, 1, 1-11; Park et al., Nano Lett. 2019, 19, 7712-7724; Zheng et al., ACS Nano 2020, 14, 12148-12158; Roxbury et al., Langmuir 2011, 27, 8282-8293).

Following the addition of 0.2% (w/v) SDBS to the different SWCNT@PEG-dendron samples, differences in the induced solvatochromic shifts were observed, as shown in FIGS. 7I-7L evaluated for the (10,2) chirality. While PEG-D-naphthoate showed the smallest wavelength shift of the (10,2) chirality of Δλ=4.1 nm, PEG-D-naphthyl showed the highest blue-shift value caused by the addition of SDBS Δλ=−16.7 nm. Both SWCNTs with aliphatic PEG-dendrons showed comparable results with a blue-shift of Δλ=−12.6 nm and −11.9 nm. It was observed that SDBS is not able to completely replace the PEG-dendrons because of their higher affinity to the SWCNTs surface, as indicated by the fluorescence spectra of the different samples after the addition of SDBS, which still differ in their resonance wavelength and relative intensity (FIGS. 6D and 7I-7L).

Example 4

Enzymatic Cleavage of PEG-Dendrons by Porcine Liver Esterase (PLE)

Figure 8A:
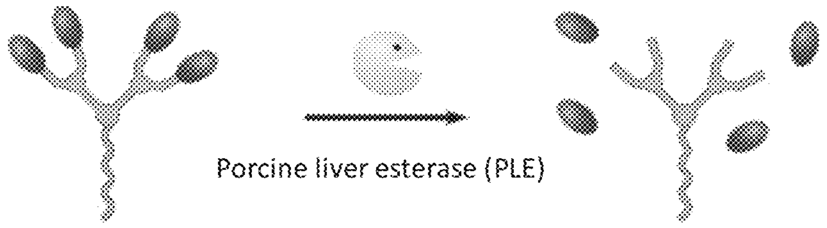
FIGS. 8A-8Q show the enzymatic cleavage of PEG-dendrons with porcine liver esterase (PLE).
Figure 8B:
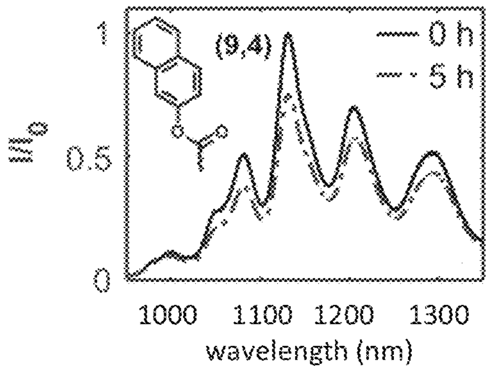
FIGS. 8B-8C show the fluorescence response of SWCNT@PEG-D-naphthyl.
Figure 8C:
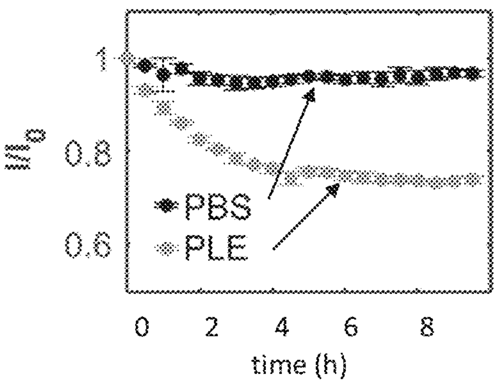
Figure 8D:
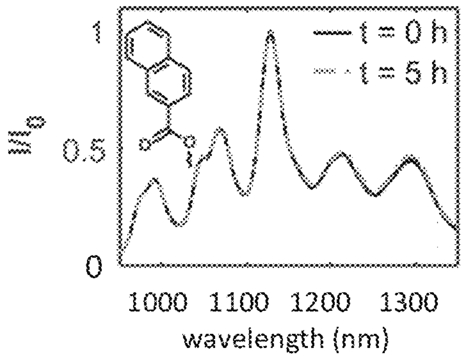
FIGS. 8D-8E show the fluorescence response of SWCNT@PEG-D-naphthoate.
Figure 8E:
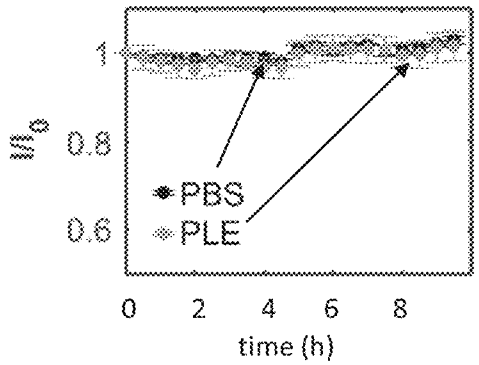
Figure 8F:
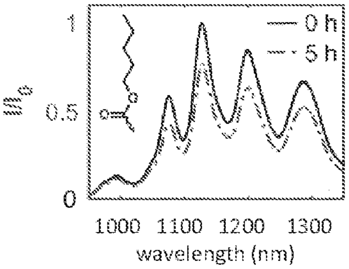
FIGS. 8F-8G show the fluorescence response of SWCNT@PEG-D-pentyl.
Figure 8G:
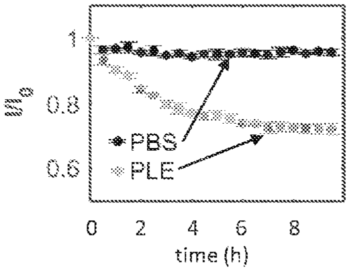
Figure 8H:
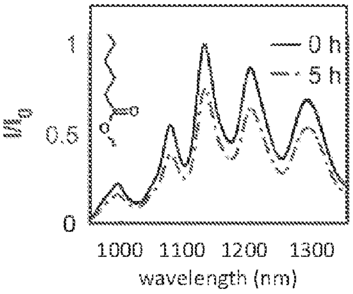
Figure 8I:
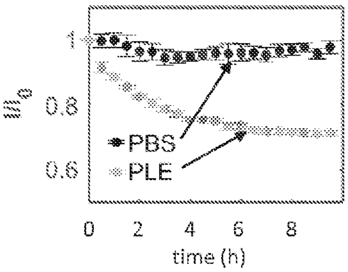
Figure 8J:
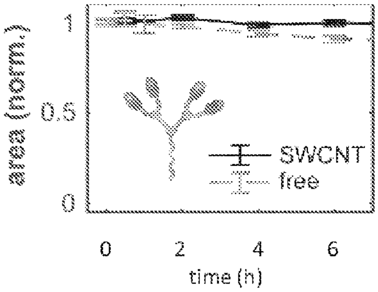
Figure 8K:
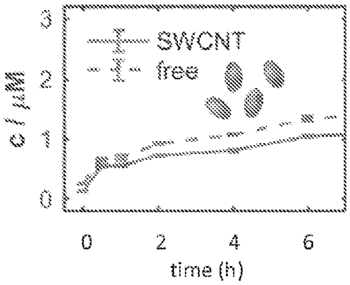
Figure 8L:
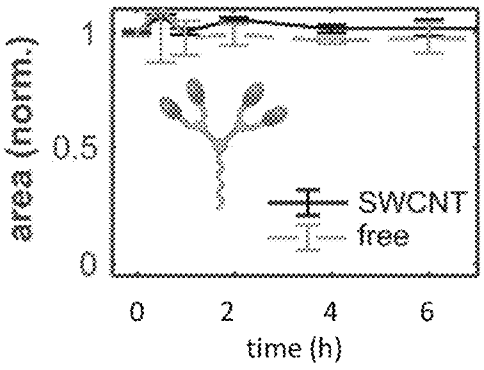
Figure 8M:
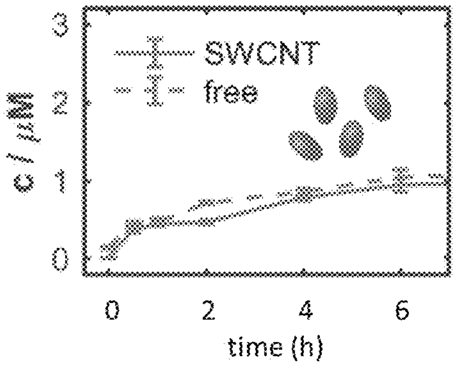
Figure 8N:
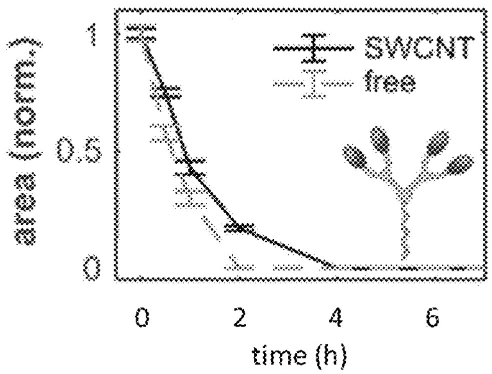
Figure 8O:
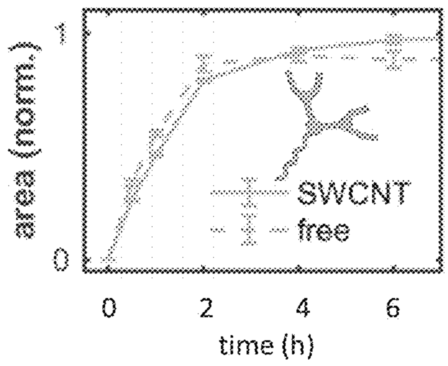
Figure 8P:
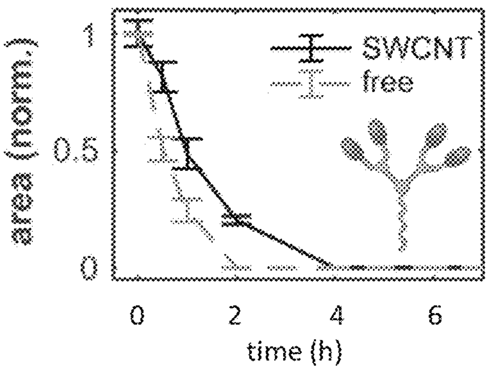
Figure 8Q:
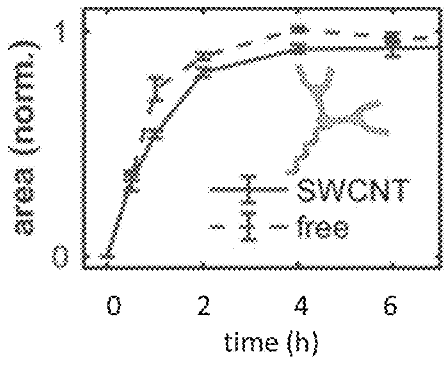

After characterizing the spectral properties of the SWCNT@PEG-dendrons, the ability to detect enzymatic cleavage of the PEG-dendrons amphiphiles by spectral response of the SWCNTs was evaluated. The variations in the fluorescence signal of the SWCNT@PEG-dendrons not only reveal different interactions between the PEG-dendrons and the SWCNT surface, but also differences in their non-covalent binding stability. The ester group connecting the hydrophobic end-groups to the dendritic branches is susceptible to enzymatic cleavage by porcine liver esterase (PLE), which can cleave off the naphthol, naphthoic acid, pentanol, and hexanoic acid end-groups (FIG. 8A), In addition to the release of these cleaved end-groups, the enzymatic cleavage should yield carboxylic acid or alcohol moieties on the dendritic block, decreasing its hydrophobicity, and thus, resulting in PEG-dendrons with a substantially-higher hydrophilic/hydrophobic ratio. The degree of enzymatic degradation of the SWCNT@PEG-dendrons depends on the non-covalent binding interactions between the nanotubes and the hydrophobic end-groups of the PEG-dendrons. In order to follow the PEG-dendron degradation, SWCNT@PEG-dendrons were incubated with PLE. The fluorescence response was monitored during an incubation time of 10 h. Significant fluorescence modulations were observed for SWCNT@PEG-D-naphthyl, SWCNT@PEG-D-pentyl, and SWCNT@PEG-D-hexanoate, showing a decrease in intensity of ca. 30%, while aliphatic PEG-dendrons showed no response (FIGS. 8J, 8L, 8N, and 8P).

Figure 9A:
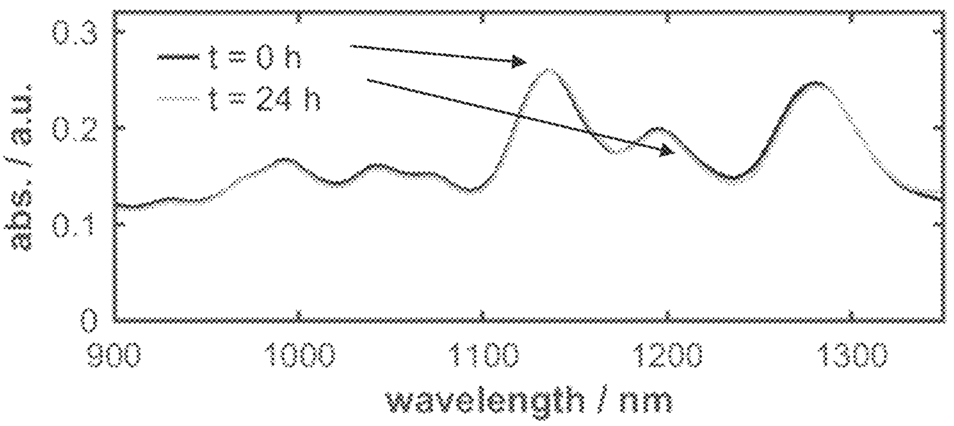
FIGS. 9A-9B show absorption of SWCNT@PEG-dendrons after incubation with PLE.
Figure 9B:
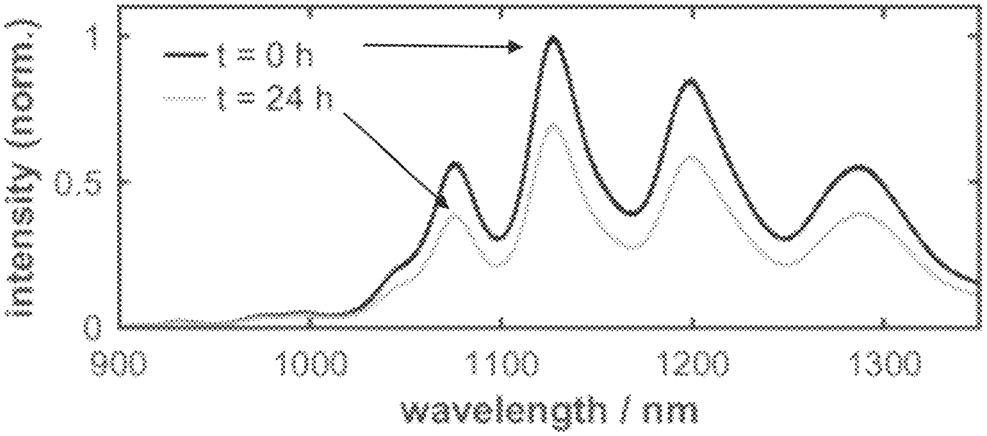
Figure 10A:
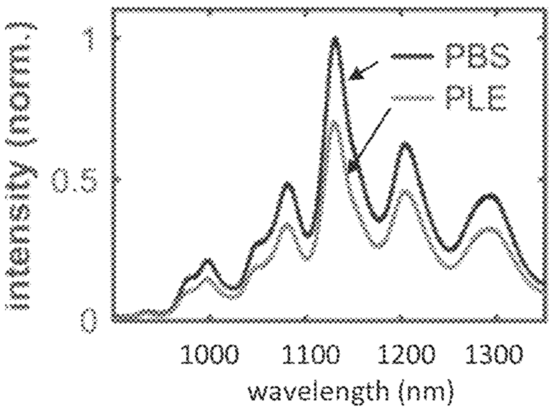
FIGS. 10A-10H show the fluorescence response of SWCNT@PEG-dendrons in the presence of PLE and BSA.
Figure 10B:
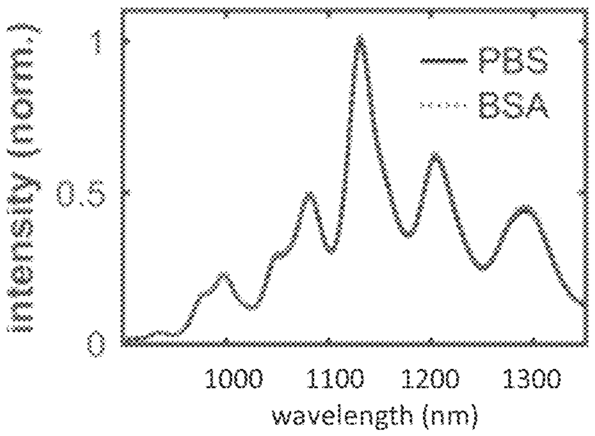
Figure 10C:
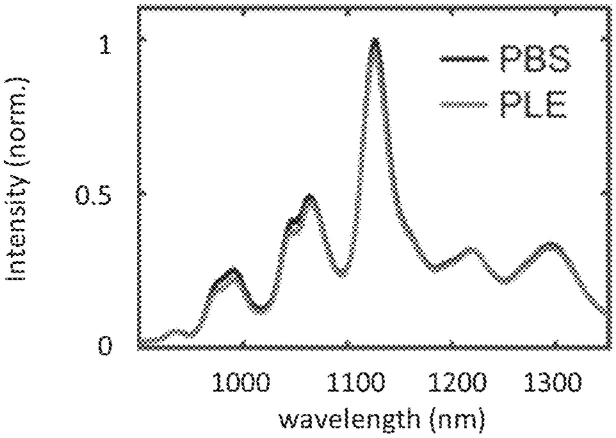
Figure 10D:
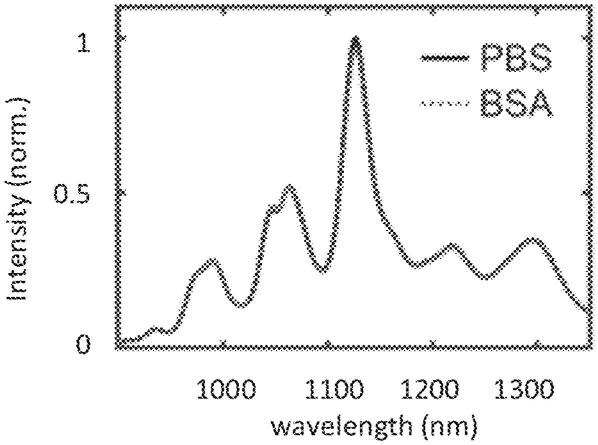
Figure 10E:
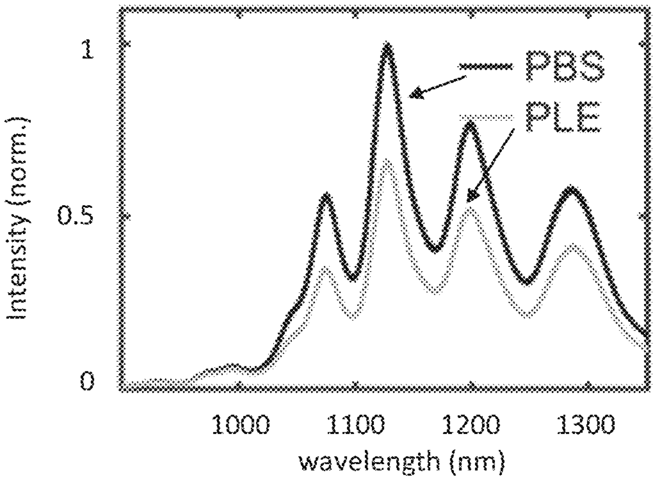
Figure 10F:
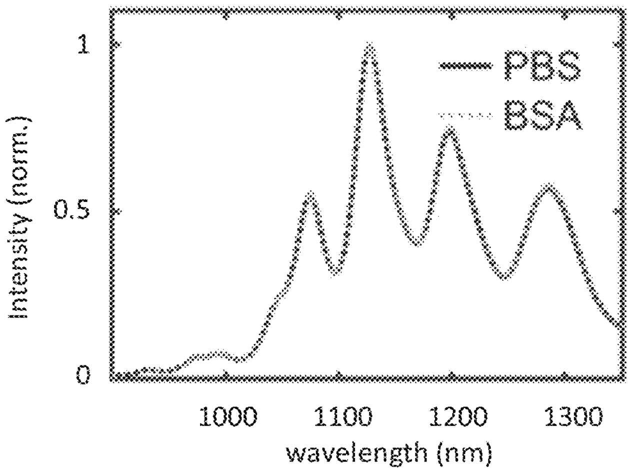
Figure 10G:
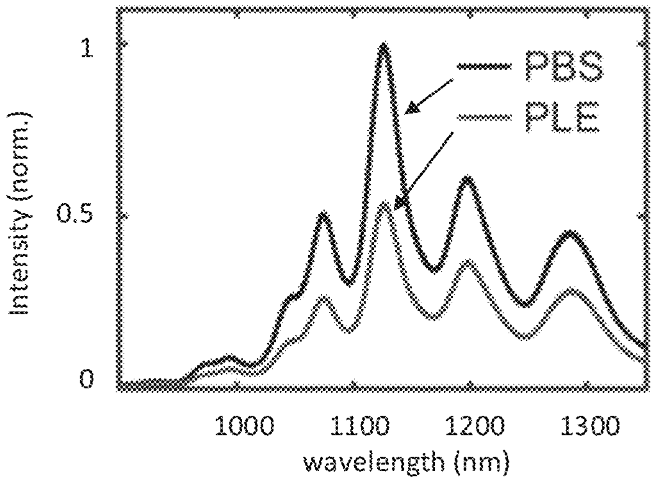
Figure 10H:
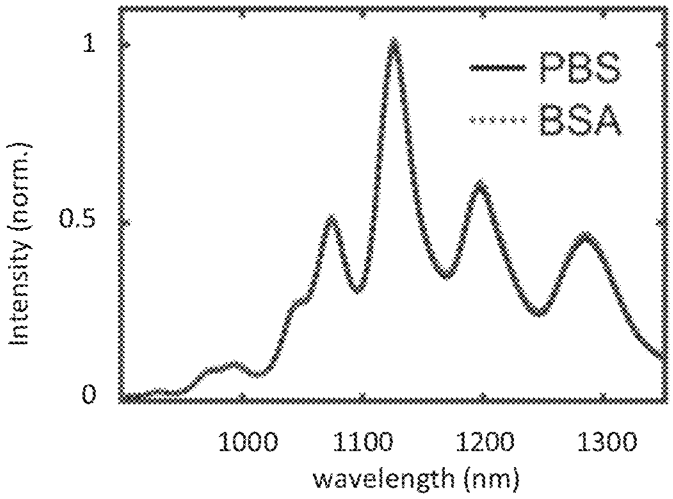
Figure 11A:
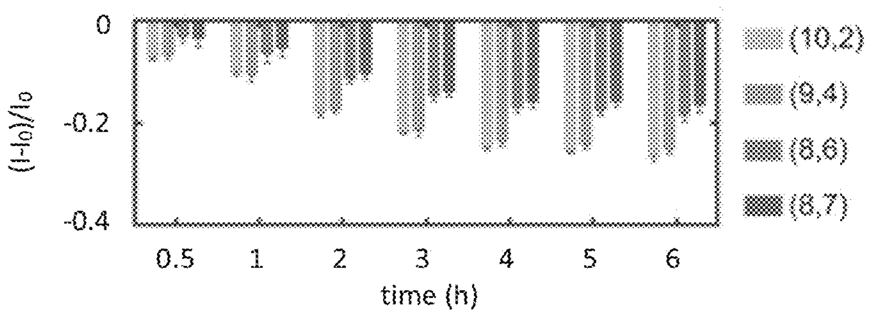
FIGS. 11A-11D show the fluorescence quenching of the different chiralities excited at =730 nm. The intensities of the chiralities denoted (10,2), (9,4), (8,6), and (8,7) are presented from left to right at each time point and were obtained by fitting the respective peaks in the spectrum.
Figure 11B:
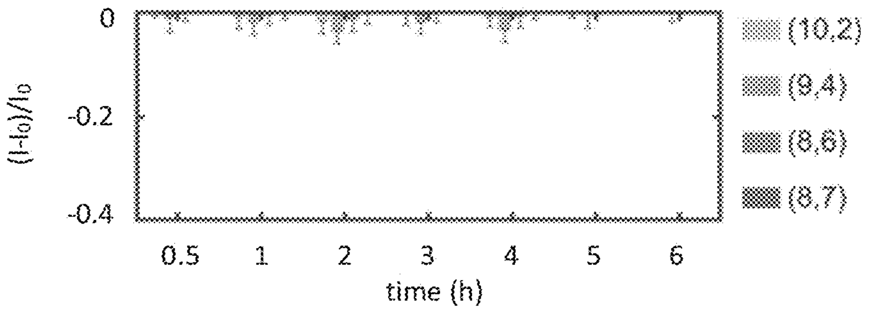
Figure 11C:
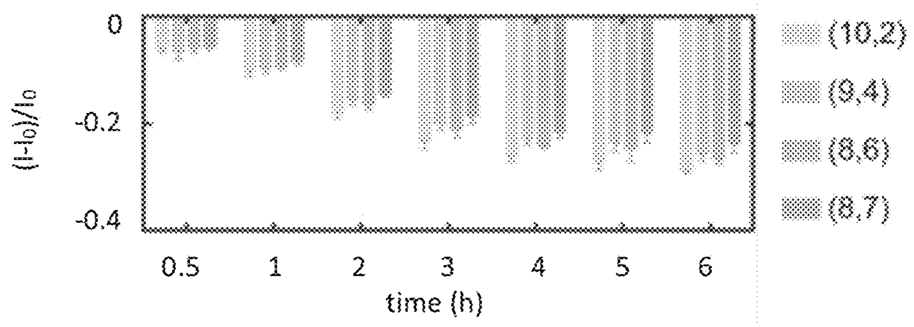
Figure 11D:
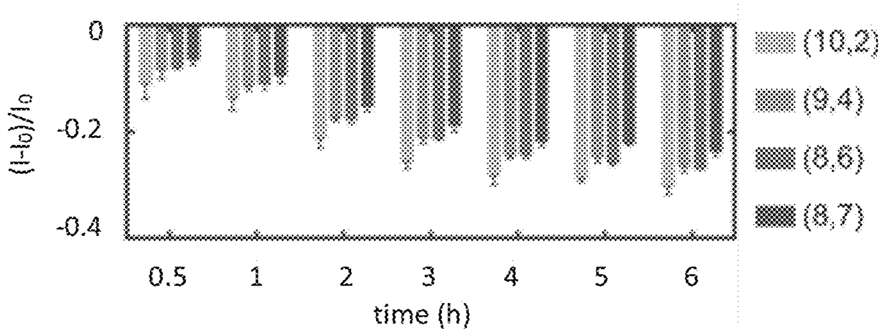

The extent of the decrease in fluorescence intensity reflects the differences in interactions between the SWCNTs and PEG-dendrons, which were mentioned above. The orientation of the ester-bond in the aromatic end-group significantly influenced the fluorescence response, as a result of the different electron density of the aromatic group. However, comparing the response of the aliphatic end-groups showed no significant differences between the two orientations. The absorption spectra of SWCNT@PEG-dendrons before and after incubation with PLE for 24 h showed no changes in absorption confirming that the fluorescence intensity decrease cannot be attributed to simple aggregation of the SWCNTs (FIG. 9A). Non-specific protein interactions with the SWCNT@PEG-dendrons were excluded as incubating them with bovine serum albumin (BSA), a protein commonly used for assays of non-specific binding, showed no fluorescence response (FIGS. 10B, 10D, 10F, and 10H). Monitoring the time-dependent fluorescence decrease of the (9,4) chirality for the different SWCNT@PEG-dendrons showed comparable decay rates for SWCNT@PEG-D-naphthyl, SWCNT@PEG-D-pentyl and SWCNT@PEG-D-hexanoate and saturation after 4-5 h (FIGS. 8K, 8M, 8O, and 8Q). Quantifying the fluorescence response of the different chiralities in each of the samples when excited at $\lambda_{ex}$=730 nm, showed a chirality dependent response (FIGS. 11A-11D and Table 3). Without being bound by any theory or mechanism of action, this may be attributed to geometrical differences in available surface area or SWCNT curvature (Wu et al., J. Phys. Chem. C 2018, 122, 7455-7463; Yurekli et al., JACS 2004, 126, 9902-9903, Salem at al., Carbon N. Y. 2016, 97, 147-153; Fagan et al., Nanoscale Adv. 201.9, 1, 3307-3324; and Zheng et al., SWCNTs, Topics in Current Chemistry Collections Springer, Cham, 2019, 129-164).

TABLE 3

| Intensity decay rate of the different chiralities | | | | |
|---|---|---|---|---|
| PEG-dendron/chirality | (10, 2) | (9, 4) | (8, 6) | (8, 7) |
| naphthyl | $-0.50\ h^{-1}$ | $-0.53\ h^{-1}$ | $-0.44\ h^{-1}$ | $-0.45\ h^{-1}$ |
| naphthoate | — | — | — | — |
| pentyl | $-0.43\ h^{-1}$ | $-0.38\ h^{-1}$ | $-0.40\ h^{-1}$ | $-0.41\ h^{-1}$ |
| hexanoate | $-0.50\ h^{-1}$ | $-0.43\ h^{-1}$ | $-0.42\ h^{-1}$ | $-0.42\ h^{-1}$ |

The mechanism governing the fluorescence response to the interactions with the esterase was studied using high performance liquid chromatography (HPLC) to directly follow and quantify the enzymatic degradation of the amphiphiles. To this end, SWCNT@PEG-dendrons were incubated with PLE at room temperature for 6 hours. During the incubation, fractions of the samples were extracted for further testing. The extracted samples were mixed with acetonitrile in a 1:1 volume ratio in order to quench the enzyme activity and precipitate the SWCNTs, while keeping the PEG-dendrons in solution. The same procedure was repeated for a comparable concentration of the PEG-dendrons in micellar assemblies in solution (50 μg $mL^{-1}$) without the nanotubes (FIGS. 2A-2D and Table 2).

Taking advantage of the ability to quantify the reaction components by HPLC, the rate of degradation of the intact PEG-dendrons, i.e., PEG-dendrons with all four end-groups (FIGS. 8J, 8L, 8N, 8P), was measured. In addition, owing to the spectroscopic signal of naphthol and naphthoic acid, which is lacking in the case of pentanol and hexanoic acid, the increasing concentration of the cleaved-off end-groups of PEG-D-naphthyl and PEG-D-naphthoate, respectively, was also measured. In case of PEG-D-pentanol and PEG-D-hexanoate, the generation of the cleaved polymer (FIGS. 8K, 8M, 8O, 8Q) was measured. For all four PEG-dendrons, the degradation process of the intact PEG-dendrons was comparable for SWCNT@PEG-dendrons and the 'free' PEG-dendrons, but slightly faster for the latter. The aromatic PEG-dendrons showed a very slow, and incomplete degradation process, as the samples still contained >95% of the intact PEG-dendrons after 6 h incubation time, in agreement with the concentration of the cleaved-off aromatic end-groups over time. Following the degradation of the intact aliphatic PEG-dendrons as well as the generation of their cleaved PEG-dendrons without end-groups, full enzymatic degradation after an incubation time of ca. 4 h was measured. Without being bound by any theory or mechanism of action, the slow degradation rate for the aromatic PEG-dendrons indicates that their micellar assemblies, as well as their binding to the SWCNT surface, are much more stable. This higher stability renders them substantially less susceptible to enzymatic degradation compared to the aliphatic hybrids.

Relating the enzymatic degradation of the PEG-dendrons to the fluorescence response of the SWCNTs, it was observed that the SWCNT@PEG-D-naphthyl had a fluorescence signal that is consistent with its end-group cleavage, while the SWCNT@PEG-D-naphthoate did not (FIGS. 12A-12D), despite having a similar concentration of cleaved end-groups (FIGS. 8J-8Q).

The significant solvatochromic shift for SWCNT@PEG-D-naphthyl upon the addition of a surfactant (FIGS. 7I-7L) indicates a large surface accessibility of the SWCNTs. Therefore, even minor changes in the corona phase of the SWCNTs, as evident from the fact that most of the PEG-D-naphthyl remains in its intact form (FIGS. 8J-8Q), can induce a strong fluorescence response. On the contrary, the PEG-D-naphthoate corona phase of the SWCNTs showed the lowest accessible surface area to surfactant perturbation (FIGS. 7I-7L) and, indeed, only a small fluorescence response upon PLE addition was observed, consistent with only a minor cleavage of the PEG-D-naphthoate observed after the separation of the reaction components via HPLC. The results obtained after the HPLC separation cannot distinguish between PEG-dendrons that were bound directly to the SWCNT surface or PEG-dendrons that are in solution, while the fluorescence signal solely monitors events in close proximity to the SWCNT surface. Hence, it is concluded that in case of the PEG-D-naphthoate, most of the cleaved-off end-groups stem from PEG-dendron molecules that are not directly bound to the SWCNTs, thus, there is no effect on the fluorescence emission of the SWCNTs.

Figure 13A:
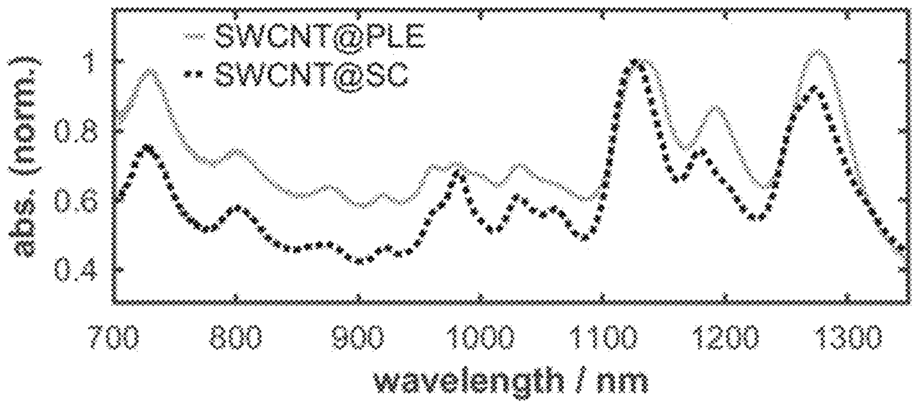
FIGS. 13A-13B show the attempts to suspend SWCNTs with PLE or the end-group hexanoic acid.
Figure 13B:
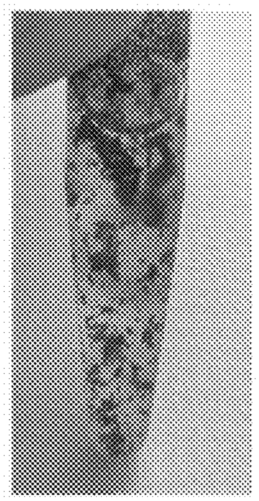

In case of the aliphatic PEG-dendrons, the fluorescence modulation of the SWCNTs as a function of time, measured by the NIR-emission of the SWCNT@PEG-dendrons, can be correlated with the generation of cleaved polymers from PEG-D-pentyl and PEG-D-hexanoate (FIGS. 12A-12D). Indeed, these PEG-dendrons revealed similar initial fluorescence modulation (FIGS. 8J-8Q), as well as similar solvatochromic shifts upon the addition of SDBS (FIGS. 7I-7L), comparable to the wavelength shift of the SWCNT@PEG-D-naphthyl. Although complete degradation of the intact aliphatic PEG-dendrons was achieved, aggregation of the SWCNT was not observed during the experiment, as the solution still contained all of the reaction components including the cleaved end-groups, the cleaved polymer, and the enzyme, the latter being partially capable of stabilizing SWCNTs in suspension, in contrary to one of the cleaved end-groups (i.e., hexanoic acid) that is incapable of stabilizing the SWCNTs (FIGS. 13A-13B).

Figure 12A:
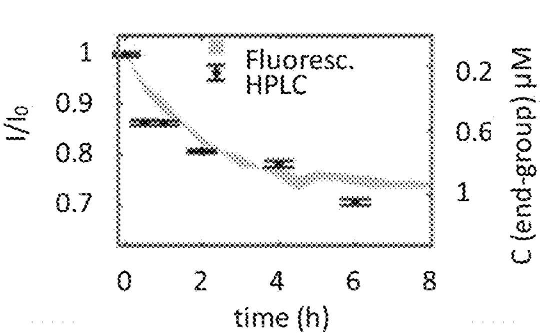
FIGS. 12A-12E show the correlation of the fluorescence signal with the degradation of the polymer-dendrons.
Figure 12B:
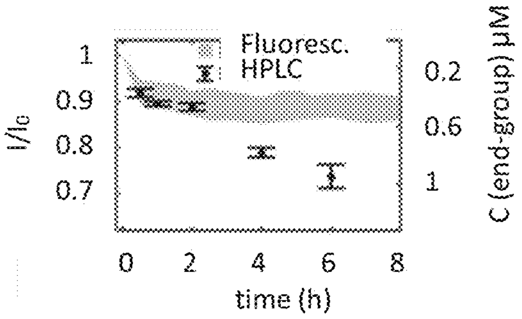
Figure 12C:
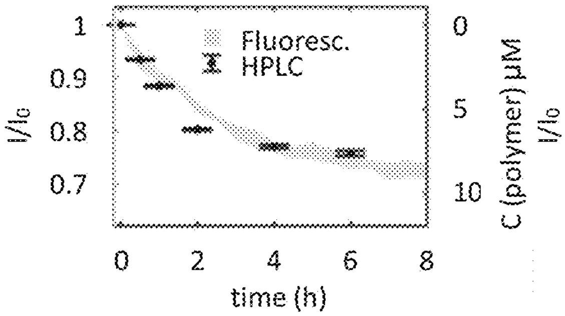
Figure 12D:
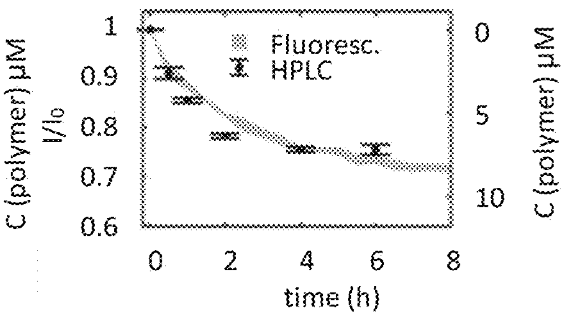
Figure 12E:
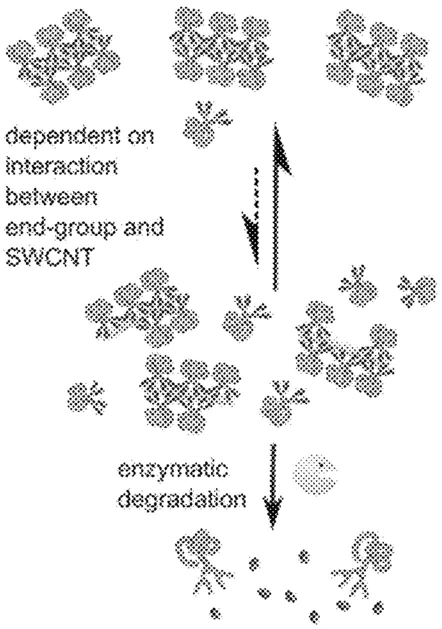

Without being bound by any theory or mechanism of action, FIG. 12E depicts a proposed mechanism for the enzymatic degradation of the PEG-dendrons coronae. Non-covalent binding of the PEG-dendrons to the SWCNTs depends on the interactions of the respective end-groups with the SWCNT surface. While aliphatic end-groups undergo full degradation, as was tracked by HPLC and could also be monitored via their fluorescence emission, the aromatic end-groups form assemblies with the SWCNTs that are much more stable but distinguished based on their specific π-π-stacking. As the rate of the enzymatic degradation is comparable for PEG-dendrons being free in solution or when bound to the SWCNTs (FIGS. 8A-8Q), the effects of the specific interactions between the different end-groups and the SWCNTs surface are solely reflected in the fluorescence response, and not in the cleavage rate. The effect of the different end-groups on the fluorescence response, on the other end, can be attributed to the available surface area probed by the induced solvatochromic shift upon surfactant addition.

Example 5

Measuring Enzymatic Activity of Penicillin G Amidase

Figure 14A:
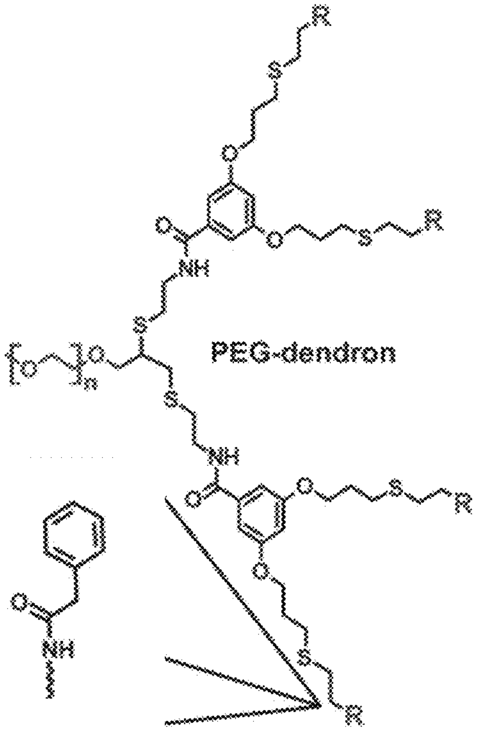
FIGS. 14A-14E show the measurement of enzymatic activity of penicillin G amidase.
Figure 14B:
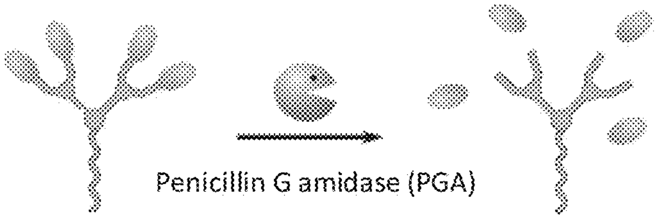
Figure 14C:
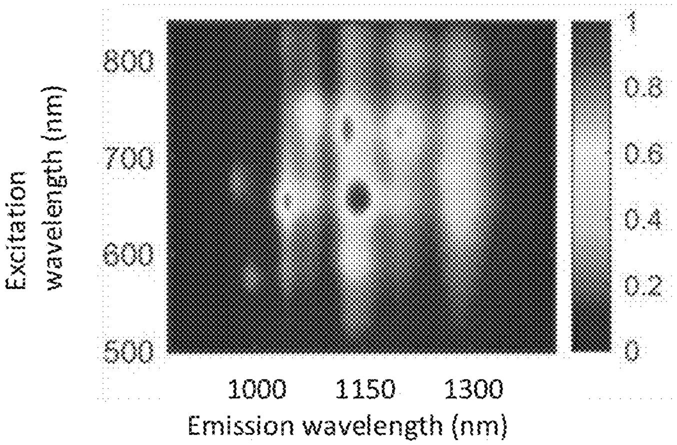
Figure 14D:
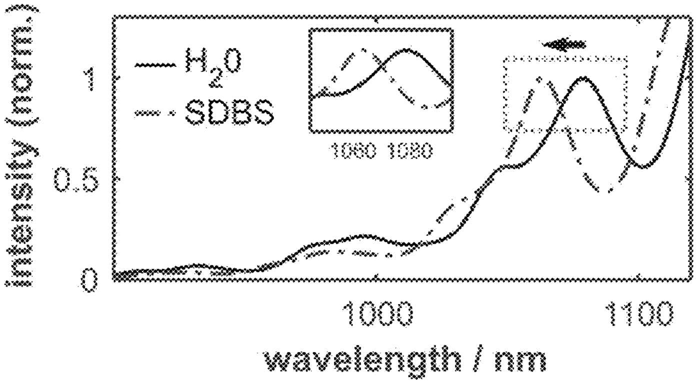
Figure 14E:
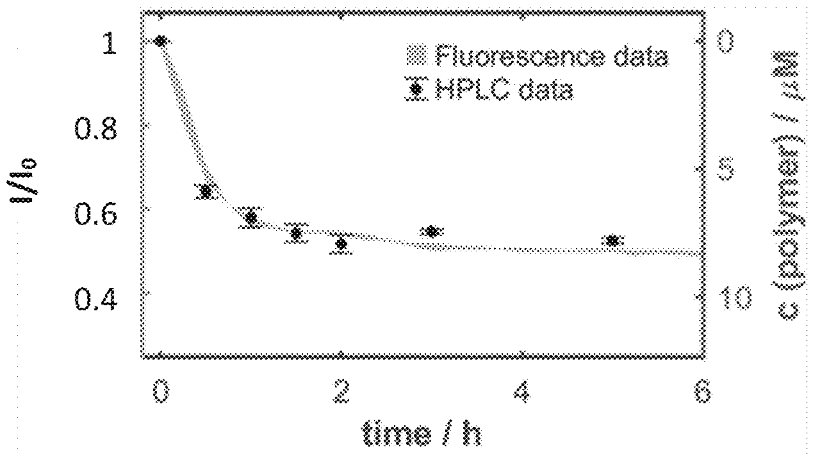

To demonstrate the generality of the SWCNT@PEG-dendrons sensing platform for enzymatic activity, penicillin G amidase (PGA), an enzyme that hydrolyses penicillin G to phenylacetic acid and 6-aminopenicillanic acid, was used. Dendrons were synthesized with a phenylacetamide end-group as a substrate for this enzyme (PEG-D-amide, FIGS. 14A-14B). Although bearing an aromatic end-group, the π-electron system of the phenylacetamide group is much smaller than that of the naphthalene-based groups. Furthermore, the carbonyl group is not conjugated to the aromatic structure and thus cannot serve as an electron withdrawing group, which could have strengthened the interaction with the electron rich SWCNTs surface, similar to the naphthoate dendron. As a result, the fluorescence modulation and the solvatochromic shift upon surfactant addition of the SWCNT@PEG-D-amide ($\Delta\lambda=-10.9$ nm) resembled the aliphatic end-groups coupled by an ester bond (FIGS. 14C-14E), suggesting a similar response to enzymatic degradation.

Figure 15:
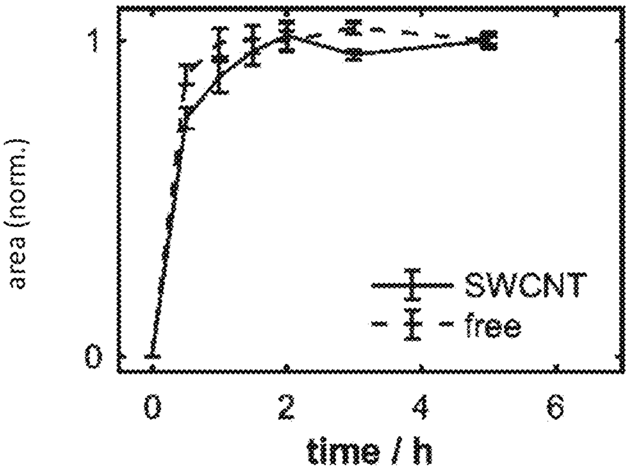
FIG. 15 shows the HPLC quantification of the degradation process of the PEG-D-amide capping SWCNTs (solid line) and as free micellar assemblies after separation (dashed line).

The time-dependent fluorescence signal of the (9,4) chirality following the addition of PGA was measured and compared to the generation of cleaved polymer after the separation via HPLC. Similar to the aliphatic PEG-dendrons, the fluorescence signal correlated well with the generation of the cleaved polymer thereby reflecting the enzymatic activity of the amidase. Comparing the amount of intact polymer before the cleavage and following 5 h of incubation with the PGA, confirmed that the polymer was completely cleaved by the enzyme. Cleavage of PEG-D-amide in the SWCNT@PEG-D-amide suspension and in free micellar assemblies in a comparable concentration (50 $\mu g\ mL^{-1}$) showed only a minute effect of the SWCNTs on the cleavage rate (FIG. 15). These experiments show, that the fluorescence modulation as well as the response of the SWCNT@PEG-dendrons towards surfactant addition provide an insight into the susceptibility of a SWCNT@PEG-dendron assembly to enzymatic degradation.

Example 6

Enzymatic Cleavage of PAA-Dendrons and PEG-Dendrons by PLE

Figure 16A:
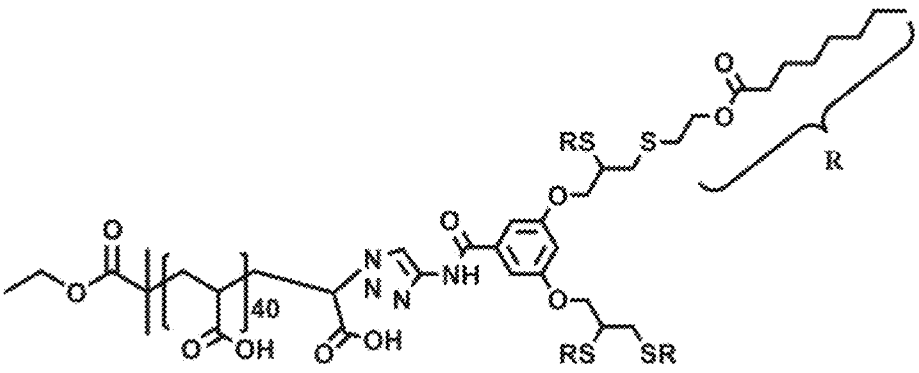
FIGS. 16A-16B show the chemical structures of additional polymer-dendron hybrids.
Figure 16B:
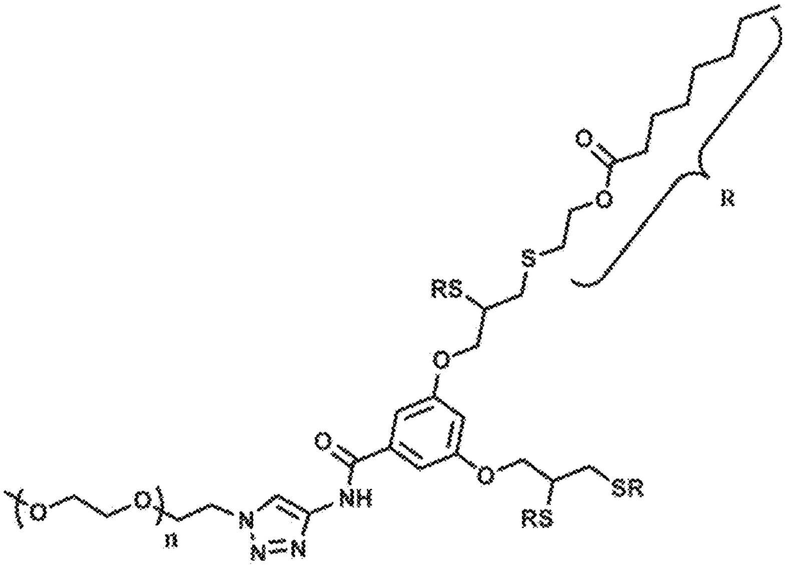
Figure 17A:
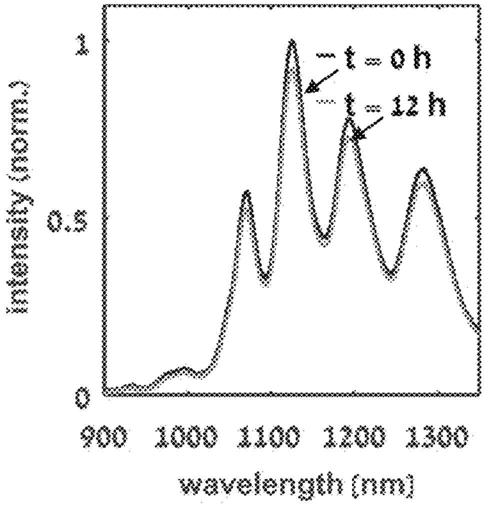
FIGS. 17A-17H show incubation of SWCNT-polymer-dendrons with esterase (PLE).
Figure 17B:
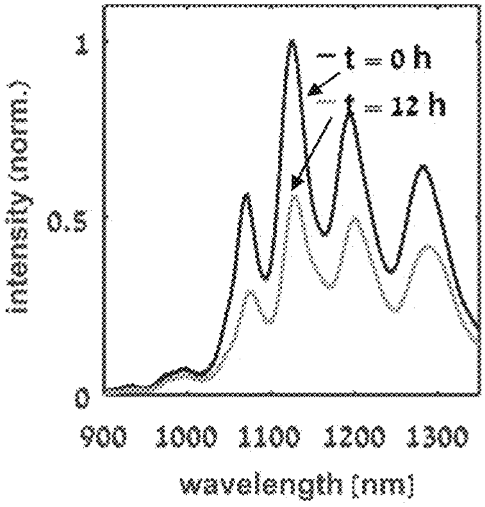
Figure 17C:
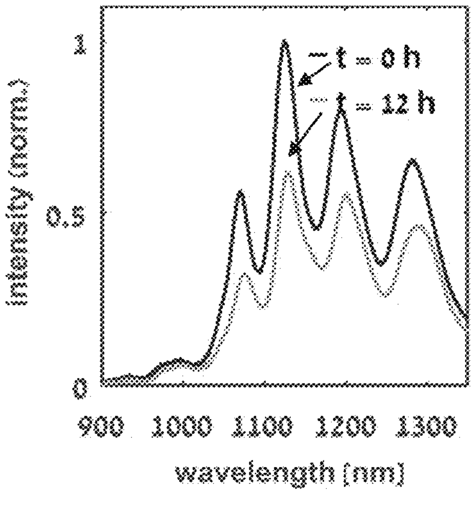
Figure 17D:
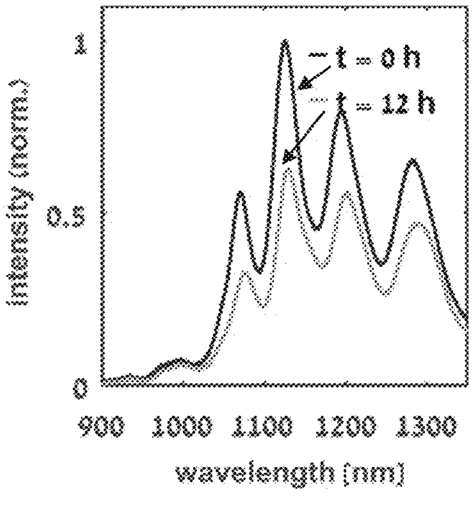
Figure 17E:
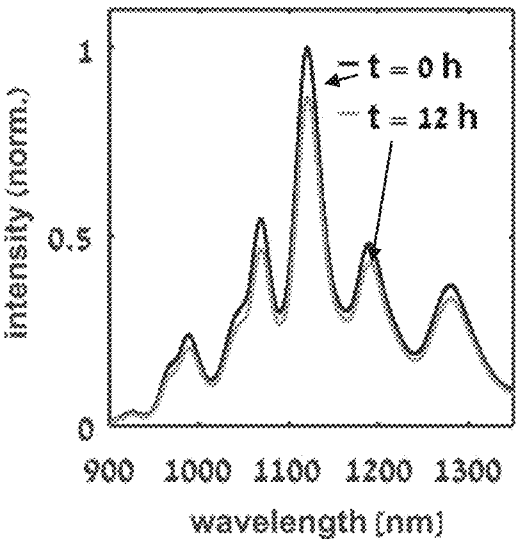
Figure 17F:
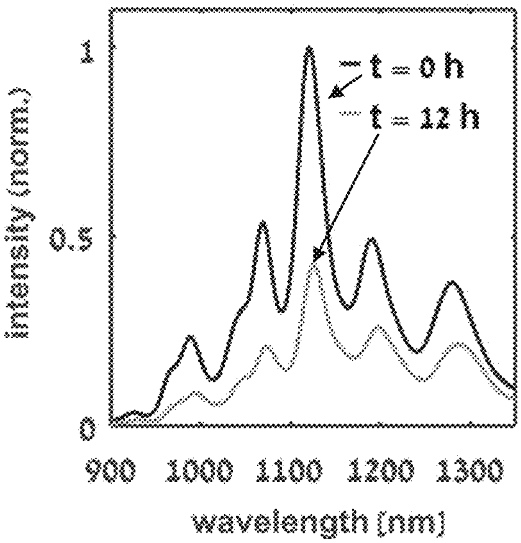
Figure 17G:
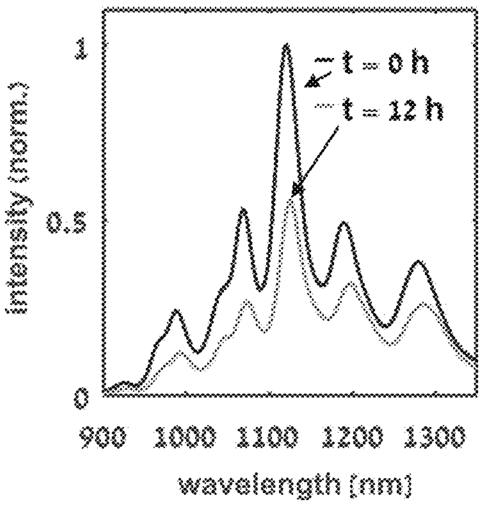
Figure 17H:
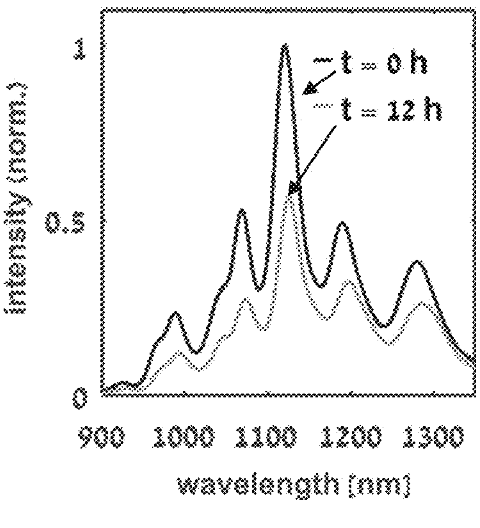
Figure 18A:
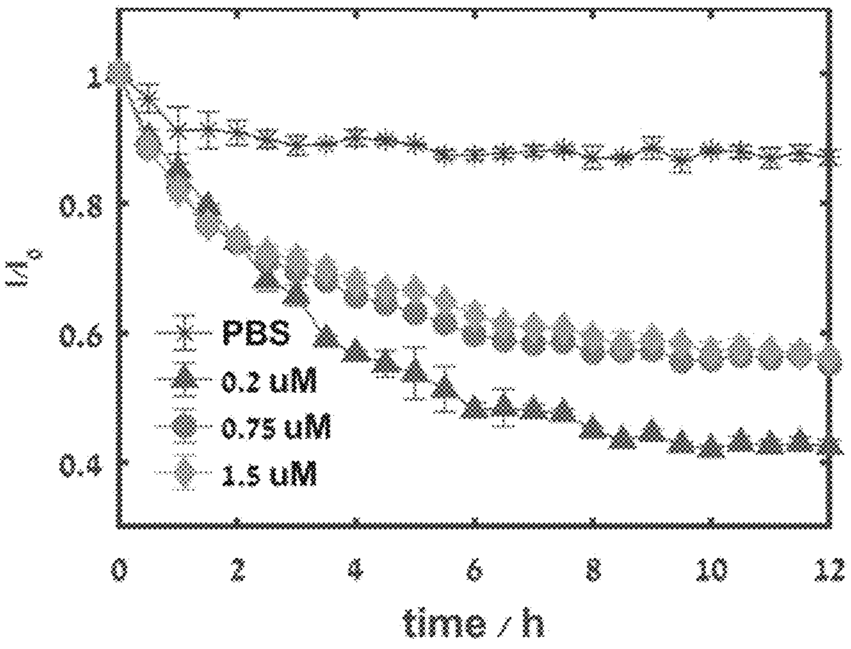
FIGS. 18A-18B show time-dependent fluorescence change of polymer-dendron functionalized SWCNTs during incubation with PLE.
Figure 18B:
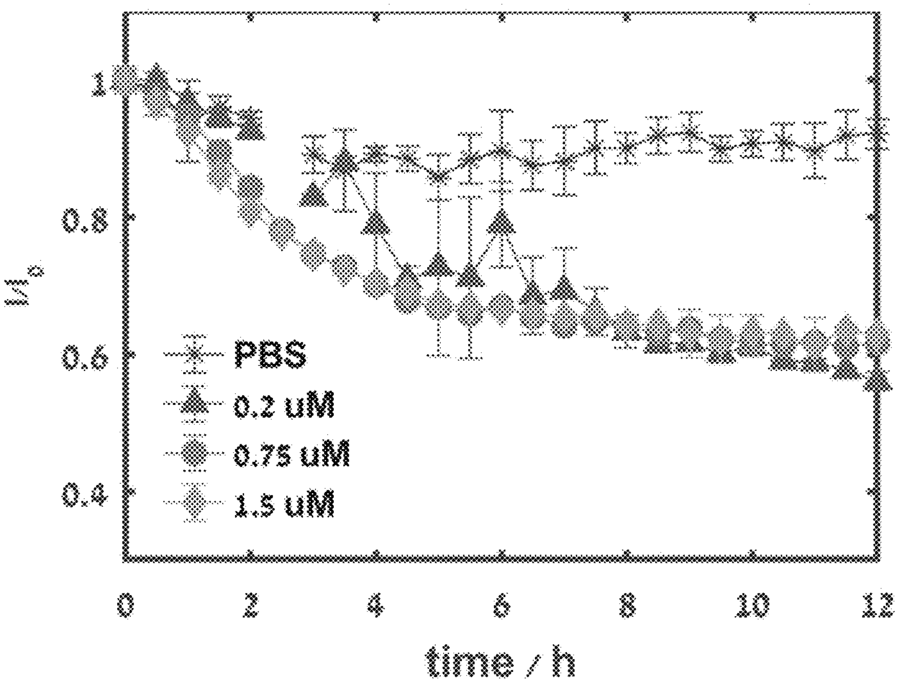

In order to substantiate the generality of the sensing platform using different dendritic hybrids, two additional hybrids were synthesized with octanoate end-groups of the dendrons and polyacrylic acid (PAA) and polyethylene glycol (PEG) hydrophilic polymers. The structures of the hybrids are depicted in FIGS. 16A and 16B.

The SWCNT@polymer-dendrons were incubated for 12 h with esterase (PLE) at different concentrations and the cleavage of the end-groups was monitored over time via the fluorescence of the SWCNTs. For both polymer-dendrons, a decrease of the fluorescence was observed following the addition of PLE (FIGS. 17A-17H, and 18A-18B).

The present invention therefore provides highly modular amphiphilic polymer-dendron hybrids, composed of hydrophobic dendrons and hydrophilic polymers that can be synthesized with a high degree of structural freedom, for suspending SWCNTs in aqueous solution. Taking advantage of the high molecular precision of these hybrids and the differences in the chemical structure of the hydrophobic end-groups of the dendrons, control of the interactions of the amphiphiles with the SWCNT surface can be obtained. These interactions can be directly related to differences in the intrinsic near-infrared fluorescence emission of the various chiralities in a SWCNT sample. Utilizing the susceptibility of the hybrids towards enzymatic degradation, the ability to monitor enzymatic activity by changes in the SWCNT fluorescent signal was demonstrated. These findings pave the way for a rational design of functional SWCNTs, which can be used for optical sensing of enzymatic activity in the near-infrared spectral range.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

The invention claimed is:

1. A complex comprising a hybrid polymer comprising a hydrophilic polymer covalently bound to a hydrophobic dendron, the dendron comprising at least one enzymatically cleavable hydrophobic end-group, and a single-walled carbon nanotube, wherein the hybrid polymer is non-covalently attached to the surface of the single-walled carbon nanotube through the at least one enzymatically cleavable hydrophobic end-group to form a corona phase capping the nanotube.

2. The complex of claim 1, wherein the hydrophilic polymer comprises polyethylene glycol (PEG), polyacrylic acid (PAA), poly(2-hydroxyethyl acrylate), or poly(oligo-ethylene glycol acrylate).

3. The complex of claim 1, wherein the hydrophilic polymer is covalently bound to the hydrophobic dendron by a group selected from the group consisting of —Z—, —$X^1$—Z—$X^2$—, —$Z^1$—$X^1$—$Z^2$—$X^2$—, wherein Z, $Z^1$, and $Z^2$ are each independently selected from $C_1$-$C_{10}$ alkylene, $C_2$-$C_{10}$ alkenylene, $C_2$-$C_{10}$ alkynylene, and arylene; $X^1$ and $X^2$ are each independently selected from —O—; —S—; —NH—; —C(═O)—; —C(═O)—O—; —O—C(═O)—O—; —C(═O)—NH—; —NH—C(═O)—NH—; —NH—C(═O)—O—; —S(═O)—; —S(═O)—O—; —PO(═O)—O—; triazolylene, and any combination thereof.

4. The complex of claim 1, wherein the hydrophobic dendron comprises between 0 to 5 generations.

5. The complex of claim 4, wherein the hydrophobic dendron comprises between 0 to 3 generations.

6. The complex of claim 4, wherein each generation of the hydrophobic dendron comprises a linear or branched $C_1$-$C_{20}$ alkylene, $C_2$-$C_{20}$ alkenylene, $C_2$-$C_{20}$ alkynylene or arylene moiety which is substituted at each end with a group selected from the group consisting of —O—, —S—, —NH—, —C(═O)—, —C(═O)—O—, —O—C(═O)—O—, —C(═O)—NH—, —NH—C(═O)—NH—, —NH—C(═O)—O—, —S(═O)—, —S(═O)—O—, —PO(═O)—O—, and any combination thereof.

7. The complex of claim 4, wherein each generation of the dendron comprises a branching unit capable of connecting between dendron generations.

8. The complex of claim 7, wherein the branching unit is an arylene which is substituted with one or more of —O—, —S—, —NH—, —C(═O)—, —C(═O)—O—, —O—C(═O)—O—, —C(═O)—NH—, —NH—C(═O)—NH—, —NH—C(═O)—O—, —S(═O)—, —S(═O)—O—, —PO(═O)—O—, and any combination thereof.

9. The complex of claim 1, wherein the hydrophobic end-group is an aromatic end-group.

10. The complex of claim 1, wherein the hydrophobic end-group is an aliphatic end-group.

11. The complex of claim 1, wherein the hydrophobic end-group is selected from the group consisting of a naphthyl group, a naphthoate group, a phenylacetamide group, a pentyl group, a hexyl group, a heptyl group, an octyl group, a nonyl group, a decyl group, a pentanoate group, a hexanoate group, a heptanoate group, an octanoate group, a nonanoate group, a decanoate group, and a phenylacetamide group.

12. The complex of claim 1, wherein the hydrophobic end-group is covalently attached to the dendron through an enzymatically cleavable functional moiety.

13. The complex of claim 12, wherein the enzymatically cleavable functional moiety is selected from the group consisting of an ester, an amide, a carbamate, a carbonate, a urea, a sulfate, an amidine, an ether, a phosphate, a phosphoamide, a sulfamate, a nitro, an azo, and a trithionate.

14. The complex of claim 12, wherein the enzymatically cleavable functional moiety is represented by the structure of —O—C(O)—R', —C(O)—OR'—NH—C(O)—R', or —C(O)—NHR' wherein R' is $C_1$-$C_{12}$ alkyl or an aryl.

15. The complex of claim 12, wherein the enzymatically cleavable functional moiety is cleavable by an amidase, an esterase, or a urease.

16. The complex of claim 1, wherein the hybrid polymer is represented by the structure depicted in any one of FIGS. 1B, 14A, 16A, and 16B.

17. The complex of claim 1, wherein the molar ratio between the hybrid polymer and the single-walled carbon nanotube ranges from about $10^6$:1 to about 100:1.

18. A method of detecting the presence of an enzyme in a sample, the method comprising the steps of:

(i) providing a complex according to claim 1;

(ii) exposing the complex to the sample; and (iii) measuring an optical property of the complex prior to and following step (ii), whereby a change in the optical property of the complex following step (ii) as compared to the optical property prior to step (ii) is indicative of the presence of the enzyme in the sample.

19. The method of claim 18, wherein the optical property comprises a fluorescence signal.

20. The method of claim 18, wherein detecting the presence of an enzyme in a sample comprises measuring enzymatic activity, monitoring enzymatic activity, or identifying the presence of a pathogen excreting an enzyme in the sample.

* * * * *